United States Patent [19]

Boschelli et al.

[11] Patent Number: 5,350,748

[45] Date of Patent: Sep. 27, 1994

[54] 3-THIO OR AMINO SUBSTITUTED-BENZO[B]THIOPHENE-2-CARBOXAMIDES AND 3-OXYGEN, THIO, OR AMINO SUBSTITUTED-BENZOFURAN-2-CARBOXAMIDES AS INHIBITORS OF CELL ADHESION

[75] Inventors: Diane H. Boschelli, Plymouth; David T. Connor, Ann Arbor, both of Mich.; James B. Kramer, Sylvania, Ohio; Paul C. Unangst, Ann Arbor, Mich.

[73] Assignee: Warner-Lambert Company, Morris Plains, N.J.

[21] Appl. No.: 108,951

[22] Filed: Aug. 18, 1993

[51] Int. Cl.$^5$ .................. A61K 31/535; A01N 43/06; C07D 413/06

[52] U.S. Cl. .................. 514/237.2; 514/233.5; 514/231.5; 514/445; 544/146

[58] Field of Search .................. 549/52, 55, 53, 54, 549/57; 514/443, 444, 445, 446, 447, 448, 237.2, 233.5, 231.5; 544/146, 145

[56] References Cited

U.S. PATENT DOCUMENTS

| | | | |
|---|---|---|---|
| 2,666,762 | 1/1954 | Cusic | 544/146 |
| 3,558,616 | 1/1971 | Brandstrom et al. | 544/146 |
| 3,622,574 | 11/1971 | Blythe et al. | 544/146 |
| 4,169,892 | 10/1979 | Robba et al. | 544/146 |
| 4,703,053 | 10/1987 | Connor et al. | 514/382 |
| 4,933,351 | 6/1990 | Atkinson et al. | 514/320 |
| 5,081,034 | 1/1992 | Bevilacqua et al. | 435/252.33 |
| 5,185,326 | 2/1993 | Müller et al. | 514/23 |
| 5,208,253 | 5/1993 | Boschelli et al. | 514/443 |
| 5,211,937 | 5/1993 | Brandley et al. | 424/1.1 |
| 5,227,369 | 7/1993 | Rosen et al. | 514/23 |

FOREIGN PATENT DOCUMENTS 9203427 5/1992 PCT Int'l Appl. .

OTHER PUBLICATIONS

*Nature* vol. 346, pp. 425–434 (1990).
*Thrombosis and Haemostasis*, 65(3), pp. 223–228 (1991).
*Clinical and Experimental Allergy*, vol. 20, pp. 619–626 (1990).
*Transplantation*, vol. 48, No. 5 pp. 727–731 (1989).
*Biochemical Pharmacology*, vol. 40, No. 8, pp. 1683–1687 (1990).
*Proc. Natl. Acad. Sci. USA*, vol. 84, pp. 9238–9242 (1987).
*J. Clin. Invest.*, vol. 82, pp. 1746–1756 (1988).
*The Journal of Immunology*, vol. 137, No. 6, pp. 1893–1896 (1986).
*Blood*, vol. 78, No. 10, pp. 2721–2726 (1991).
*Proc. Natl. Acad. Sci. USA*, vol. 83, pp. 1911–1915 (1986).

Primary Examiner—Richard L. Raymond
Assistant Examiner—Deborah Lambkin
Attorney, Agent, or Firm—Ronald A. Daignault; Charles W. Ashbrook

[57] ABSTRACT

3-Thio or amino substituted benzo[b]thiophene-2-carboxamides and 3-oxygen, thio, or amino substituted benzofuran-2-carboxamides are described as agents which inhibit leukocyte adherence to vascular endothelium and, as such, are effective therapeutic agents for treating inflammatory diseases. Certain of these compounds are novel and methods of manufacture are also described.

The same benzo[b]thiophene and benzofuran-2-carboxamides also inhibit the activation of human immunodeficiency virus (HIV), latent in infected mammals.

3 Claims, No Drawings

3-THIO OR AMINO SUBSTITUTED-BENZO[B]THIOPHENE-2-CARBOXAMIDES AND 3-OXYGEN, THIO, OR AMINO SUBSTITUTED-BENZOFURAN-2-CARBOXAMIDES AS INHIBITORS OF CELL ADHESION

BACKGROUND OF THE INVENTION

The present invention is for the use of 3-thiol, thioether, amino, alkylamino, or arylamino-benzo[b]thiophene-2-carboxamides, and 3-alkoxy, aryloxy, thiol, thioether, amino, alkylamino, or arylamino-benzofuran-2-carboxamides, and pharmaceutically acceptable salts thereof, to prevent the adhesion of leukocytes to endothelial cells. Leukocyte adherence to vascular endothelium is integral to the pathogenesis of inflammation. The adhesion process precedes transendothelial migration of leukocytes into surrounding tissue and ensuing tissue damage. Compounds that can block this initial adhesive interaction are expected to have efficacy in the treatment of inflammatory diseases such as rheumatoid arthritis, asthma, and psoriasis. Other indications would include, but are not limited to, adult respiratory distress syndrome, reperfusion injury, ischemia, ulcerative colitis, vasculitides, atherosclerosis, inflammatory bowel disease, and tumor metastases.

Adhesion receptors are organized into three main families: the selectins, the immunoglobulin superfamily, and the integrins [Nature 346, 426 (1990)]. Members of all three classes are involved in mediating leukocyte adhesion during inflammation [for reviews of this area see: Thrombosis and Hemostasis 65(3), 223 (1991); Clinical and Experimental Allergy 20, 619 (1990); Transplantation 48, 727 (1989); Biochemical Pharm. 40(8), 1683 (1990)]. Endothelial leukocyte adhesion molecule-1 (ELAM-1 or E-selectin) is a member of the selectin family of glycoproteins that promote cell-cell adhesion. ELAM-1 is reported to be maximally expressed on the surface of endothelial cells 4 hours after stimulation of the endothelial cells with cytokines, such as interleukin-1 (IL-1) or tumor necrosis factor α (TNF-α) or other inflammatory mediators, such as lipopolysaccharide (LPS) [Pro. Nat. Acad. Sci. 84, 9238 (1987)].

Intercellular adhesion molecule-1 (ICAM-1) is a member of the immunoglobulin superfamily. It is also upregulated with maximum expression occurring 12 to 24 hours after stimulus. It has been shown that 4 hours after the endothelial cells are stimulated with an inflammatory mediator, both ELAM-1 and ICAM-1 are present on the cell surface [J. Clin. Invest. 82, 1746 (1988) and J. Immun. 137, 1893 (1986); Blood 78, 2721 (1991)].

The 3-thiol, thioether, amino, alkylamino, or arylamino-benzo[b]thiophene-2-carboxamides and 3-alkoxy, aryloxy, thiol, thioether, amino, alkylamino, or arylamino-benzofuran-2-carboxamides have been shown in an in vitro assay to prevent the adhesion of neutrophils to human umbilical vein endothelial cells (HUVECS) stimulated with TNF-α. In this assay, HUVECS are stimulated with TNF-α for 4 hours, after which the cells are assayed for their ability to adhere to human neutrophils labeled with either $^{51}Cr$ or calcein, a fluorescent dye. The results obtained are shown in Tables 1-2. The details of this assay are described in the DETAILED DESCRIPTION.

Several of the 3-substituted-benzo[b]thiophene-2-carboxamides and 3-substituted-benzofuran-2-carboxamides contained here are included in the generic scope of U.S. Pat. No. 4,933,351, which claims these compounds as inhibitors of 5-lipoxygenase for the treatment of allergy, asthma, and inflammation, and/or in the generic scope of WO 9203-427 A, which claims these compounds as hypercalcaemic agents for the treatment of osteoporosis.

3-Alkoxy, aryloxy-, and arylalkyloxy-benzo[b]-thiophene-2-carboxamides are described in U.S. Pat. No. 5,208,253 as inhibitors of cell adhesion.

The present invention also relates to the above 3-substituted-benzo[b]thiophene- and benzofuran-2-carboxamides which inhibit the activation of human immunodeficiency virus (HIV), latent in infected mammals.

The pathogenesis of the human immunodeficiency virus (HIV) is complicated and as of yet not completely understood. The virus life cycle has theoretically been divided into afferent and efferent components. Virus binding, fusion, reverse transcription, and finally integration are among those events which encompass the afferent component of the life cycle. It is the afferent component of the HIV life cycle which is responsible for primary infection of HIV in an individual, generally followed by a burst of viraemia with or without clinical symptoms.

Many therapeutic strategies have been developed and targeted for intervention during the afferent events. See for example, Mitsuya H, Broder S. "Inhibition of the In Vitro Infectivity and Cytopathic Effect on Human T-Lymphotropic Virus Type III/Lymphadenopathy Virus-Associated Virus (HTLV-III/LAV) by 2',3'-Dideoxynucleosides." Proc. Natl. Acad. Sci (USA) 83, 1911–1915 (1986).

Whereas different stages of the afferent component offer the potential for effective therapeutic intervention, it has become increasingly apparent that intervention solely at these points is insufficient. After becoming infected with HIV and the disease progresses through the afferent stages, an individual experiences a prolonged period of clinical latency which may extend for several years and the individual remains in good health. At this point in time, low to absent levels of viraemia and virus replication in peripheral blood cells are achieved. At a later point, however, the disease eventually progresses to life-threatening immunosuppression (AIDS) for which there remains no cure. These later events are the clinical manifestations of the efferent stages of HIV infection.

The efferent component of the HIV life cycle includes those events necessary for the HIV provirus to successfully transcribe, translate, assemble, and produce virions. Onset of the events necessary for HIV-infected cells to progress from an asymptomatic, non-HIV expressive stage to a symptomatic, HIV expressive stage is referred to as activation. Presently, the efferent component and the cellular basis for activation is not completely understood. Nevertheless, if novel therapeutic agents and strategies are developed and implemented during the clinically asymptomatic phase to fight the progression toward AIDS, some hope may be afforded the estimated one million infected, but clinically asymptomatic individuals.

While the above 3-substituted-benzo[b]thiophene- and benzofuran-2-carboxamides have already generally been described, the present invention includes certain novel compounds and, more importantly, includes novel therapeutic uses for those already known compounds.

SUMMARY OF THE INVENTION

Accordingly, the present invention is for the use of a compound of the formula (I) or (II) to inhibit the adhesion of leukocytes to stimulated human endothelial cells, thereby providing for the treatment of inflammatory diseases:

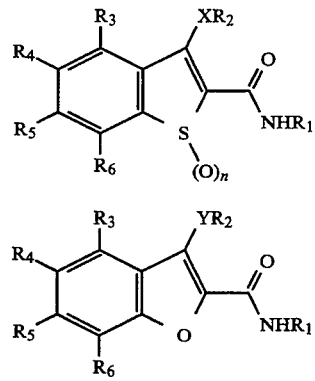

wherein $R_1$ is hydrogen; lower alkyl, or lower alkyl substituted by halogen; phenyl, or phenyl substituted by hydroxy, halogen, lower alkyl, lower alkoxy, or $CO_2R_7$ where $R_7$ is hydrogen or lower alkyl; benzyl, or benzyl substituted by hydroxy, halogen, lower alkyl, lower alkoxy, or $CO_2R_7$ as defined above;

$R_2$ is hydrogen, lower alkyl, phenyl, benzyl, substituted lower alkyl as defined above, substituted phenyl as defined above, substituted benzyl as defined above, or $—(CH_2)_mQ$ in which Q is $CO_2R_7$ as defined above or a 5- or 6-membered saturated or unsaturated heterocyclic ring containing up to 3 heteroatoms selected from nitrogen, oxygen, and sulfur;

n is an integer from 0 to 2;

m is an integer from 0 to 6;

X is $S(O)_n$ or $NR_2$ in which $R_2$ is defined above; and $R_3$, $R_4$, $R_5$, and $R_6$ are each independently hydrogen, hydroxy, halogen, lower alkyl, trifluoromethyl, lower alkoxy, phenyl, benzyloxy, nitro, or $—NR_7R_2$ in which $R_7$ and $R_2$ are as defined above; or a pharmaceutically acceptable acid addition or base salt thereof.

In a compound of formula (II), Y is O, $S(O)_n$, or $NR_2$ in which $R_2$ is as defined above, but excluding a compound of formula (II) where Y is 0 and $R_2$ is hydrogen.

Preferred compounds of formula (I) are those wherein $R_1$ is hydrogen, lower alkyl, phenyl or benzyl in which phenyl or benzyl is unsubstituted or substituted by $—CO_2R_7$;

$R_2$ is hydrogen, lower alkyl, phenyl or benzyl in which phenyl or benzyl is unsubstituted or substituted by $—CO_2R_7$ or $—(CH_2)_mQ$ in which Q is $—CO_2R_7$ or morpholine.

Particularly valuable compounds of formula (I) are:

5-methoxy-3-[(1-methylethyl)thio]benzo[b]thiophene-2-carboxamide,
3-[(1-methylethyl)thio]benzo[b]thiophene-2-carboxamide,
5-methoxy-3-[(1-methylethyl)sulfonyl]benzo[b]thiophene-2-carboxamide,
5-methoxy-3-(methylthio)benzo[b]thiophene-2-carboxamide,
5-methoxy-3-(phenylthio)benzo[b]thiophene-2-carboxamide,
5-methoxy-3-(phenylmethyl)thio]benzo[b]thiophene-2-carboxamide,
methyl4-[[[5-methoxy-3-[(methylethyl)thio]benzo[b]thien-2yl]carbonyl]amino]benzoate,
4-[[[5-methoxy-3-[(1-methylethyl)thio]benzo[b]thien-2yl]carbonyl]amino]benzoic acid,
3-mercapto-5-methoxybenzo[b]thiophene-2-carboxamide,
methyl3-[[2-(aminocarbonyl)-5-methoxybenzo[b]thien-3-yl]thio]propanoate,
5-methoxy-3-[[2-(4-morpholinyl)ethyl]thio]benzo[b]thiophene-2-carboxamide,
4-chloro-3-[(1-methylethyl)thio]benzo[b]thiophene-2-carboxamide,
methyl 3-[[2-(aminocarbonyl)-5-methoxybenzo[b]thien-3-yl]thio]pentanoate,
5-[[2-(aminocarbonyl)-5-methoxybenzo[b]thien-3-yl]thio]pentanoic acid,
[[2-(aminocarbonyl)-5-methoxybenzo[b]thien-3-yl]thio]acetic acid,
methyl4-[[[2-(aminocarbonyl)-5-methoxybenzo[b]thien-3-yl]thio]methyl]benzoate,
3-[(1-methylethyl)thio]-5-(phenylmethoxy)benzo[b]thiophene-2-carboxamide,
4-chloro-3-(dimethylamino)benzo[b]thiophene-2-carboxamide,
3-amino-4-methoxybenzo[b]thiophene-2-carboxamide,
3-(dimethylamino)-4-methoxybenzo[b]thiophene-2-carboxamide,
3-(dimethylamino)-5-(methylthio)benzo[b]thiophene-2-carboxamide,
5-methoxy-3-(methylamino)benzo[b]thiophene-2-carboxamide-1-oxide,
5-methoxy-3-[(1-methylethyl)amino]benzo[b]thiophene-2-carboxamide-1-oxide, and
5-methoxy-3-(phenylamino)benzo[b]thiophene-2-carboxamide-1-oxide.

Preferred compounds of formula (II) are those wherein $R_1$ is hydrogen, lower alkyl, phenyl, or benzyl; $R_2$ is hydrogen, lower alkyl, or benzyl; and Y is O or $NR_2$.

Particularly valuable compounds of formula (II) are:

3-amino-2-benzofurancarboxamide,
3-amino-4-chloro-2-benzofurancarboxamide,
5-methoxy-3-(1-methylethoxy)-2-benzofurancarboxamide,
5-chloro-3-(1-methylethoxy)-2-benzofurancarboxamide,
3-(1-methylethoxy)-2-benzofurancarboxamide,
5-methoxy-3-(1-methylethoxy)-N-(phenylmethyl)-2-benzofurancarboxamide,
5-chloro-3-(1-methylethoxy)-N-phenyl-2-benzofurancarboxamide,
5-chloro-3-(1-methylethoxy)-N-(phenylmethyl)-2-benzofurancarboxamide,
3-(1-methylethoxy)-N-(1-methylethyl)-2-benzofurancarboxamide,
3-(1-methylethoxy)-N-phenyl-2-benzofurancarboxamide,
3-(1-methylethoxy)-N-(phenylmethyl)-2-benzofurancarboxamide, 5-hydroxy-3-(1-methylethoxy)-2-benzofurancarboxamide, 5-methoxy-3-(phenylmethoxy)-2-benzofurancarboxamide, and 3-(1-methylethoxy)-5-phenyl-2-benzofurancarboxamide.

A second aspect of the present invention is the use of a compound of the formula (I) or (II) to inhibit the activation of HIV, latent in infected mammals, thereby providing for the treatment of AIDS:

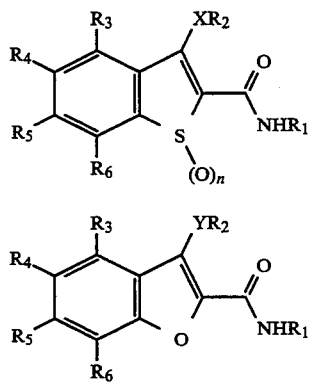

wherein $R_1$ is hydrogen; lower alkyl, or lower alkyl substituted by halogen; phenyl or phenyl substituted by hydroxy, halogen, lower alkyl, lower alkoxy, or $CO_2R_7$ where $R_7$ is hydrogen or lower alkyl; benzyl, or benzyl substituted by hydroxy, halogen, lower alkyl, lower alkoxy, or $CO_2R_7$ as defined above;

$R_2$ is hydrogen, lower alkyl, phenyl, benzyl, substituted lower alkyl as defined above, substituted phenyl as defined above, substituted benzyl as defined above, or —$(CH_2)_mQ$ in which Q is $CO_2R_7$ as defined above or a 5- or 6-membered saturated or unsaturated heterocyclic ring containing up to 3 heteroatoms selected from nitrogen, oxygen, and sulfur;

n is an integer from 0 to 2;

m is an integer from 0 to 6;

X is $S(O)_n$ or $NR_2$ in which $R_2$ is as defined above; and $R_3$, $R_4$, $R_5$, and $R_6$ are each independently hydrogen, hydroxy, halogen, lower alkyl, trifluoromethyl, lower alkoxy, phenyl, benzyloxy, nitro, or —$NR_7R_2$ in which $R_7$ and $R_2$ are as defined above; or a pharmaceutically acceptable acid addition or base salt thereof.

In a compound of formula (II), Y is O, $S(O)_n$, or $NR_2$ in which $R_2$ is as defined above, but excluding a compound of formula (II) where Y is O and $R_2$ is hydrogen.

Particularly preferred is the use of 5-methoxy-3-[(1-methylethyl)thio]benzo[b]thiophene-2-carboxamide to treat AIDS by administering an effective amount of the compound in unit dosage form.

A third aspect of the present invention are the following novel compounds:

5-methoxy-3-[(1-methylethyl)thio]benzo[b]thiophene-2-carboxamide,

3-[(1-methylethyl)thio]benzo[b]thiophene-2-carboxamide, 5-methoxy-3-[(1-methylethyl)sulfonyl]benzo[b]thiophene-2-carboxamide, 5-methoxy-3-(methylthio)benzo[b]thiophene-2-carboxamide, 5-methoxy-3-(phenylthio)benzo[b]thiophene-2-carboxamide, 5-methoxy-3-(phenylmethyl)thio]benzo[b]thiophene-2-carboxamide, methyl 4-[[[5-methoxy-3-[(methylethyl)thio]benzo[b]thien-2-yl]carbonyl]amino]benzoate, 4-[[[5-methoxy-3-[(1-methylethyl)thio]benzo[b]thien-2yl]carbonyl]amino]benzoic acid, 3-mercapto-5-methoxybenzo[b]thiophene-2-carboxamide, methyl 3-[[2-(aminocarbonyl)-5-methoxybenzo[b]thien-3-yl]thio]propanoate, 5-methoxy-3-[[2-(4-morpholinyl)ethyl]thio]benzo[b]thiophene-2-carboxamide, 4-chloro-3-[(1-methylethyl)thio]benzo[b]thiophene-2-carboxamide, methyl 3-[[2-(aminocarbonyl)-5-methoxybenzo[b]thien-3-yl]thio]pentanoate, 5-[[2-(aminocarbonyl)-5-methoxybenzo[b]thien-3-yl]thio]pentanoic acid,

[[2-(aminocarbonyl)-5-methoxybenzo[b]thien-3-yl]thio]acetic acid, methyl 4-[[[2-(aminocarbonyl)-5-methoxybenzo[b]thien-3-yl]thio]methyl]benzoate, 3-[(1-methylethyl)thio]-5-(phenylmethoxy)benzo[b]thiophene-2-carboxamide, 4-chloro-3-(dimethylamino)benzo[b]thiophene-2-carboxamide, 3-amino-4-methoxybenzo[b]thiophene-2-carboxamide, 3-(dimethylamino)-4-methoxybenzo[b]thiophene-2-carboxamide, 3-(dimethylamino)-5-(methylthio)benzo[b]thiophene-2-carboxamide, 5-methoxy-3-(methylamino)benzo[b]thiophene-2-carboxamide-1-oxide, 5-methoxy-3[(1-methylethyl)amino]benzo[b]thiophene-2-carboxamide-1-oxide, 5-methoxy-3-(phenylamino)benzo[b]thiophene-2-carboxamide-1-oxide, 5-methoxy-3-(1-methylethoxy)-2-benzofurancarboxamide, 5-chloro-3-(1-methylethoxy)-2-benzofurancarboxamide, 3-(1-methylethoxy)-2-benzofurancarboxamide, 5-methoxy-3-(1-methylethoxy)-N-(phenylmethyl)-2-benzofurancarboxamide, 5-chloro-3-(1-methylethoxy)-N-phenyl-2-benzofurancarboxamide, 5-chloro-3-(1-methylethoxy)-N-(phenylmethyl)-2-benzofurancarboxamide, 5-hydroxy-3-(1-methylethoxy)-2-benzofurancarboxamide, 3-(1-methylethoxy)-N-(1-methylethyl)-2-benzofurancarboxamide, 3-(1-methylethoxy)-N-phenyl-2-benzofurancarboxamide, 3-(1-methylethoxy)-N-(phenylmethyl)-2-benzofurancarboxamide, 5-methoxy-3-(phenylmethoxy)-2-benzofurancarboxamide, and 3-(1-methylethoxy)-5-phenyl-2-benzofurancarboxamide, or a pharmaceutically acceptable acid addition or base salt thereof.

DETAILED DESCRIPTION

The terms used in defining the compounds of Formulas I and II and the more particular compounds of the present invention are defined as follows:

Lower alkyl and lower alkoxy mean a straight or branched alkyl or alkoxy group having 1to 6 carbon atoms and includes, for example, methyl, ethyl, propyl, i-propyl, or otherwise referred to as (methyl)ethyl, and t-butyl or otherwise referred to as 1,1-(dimethyl)ethyl, and correspondingly, for example, methoxy, ethoxy, i-propoxy, or otherwise referred to as 1-(methyl)ethoxy and the like.

Halogen includes fluorine, chlorine, bromine, or iodine.

A 5- or 6-membered saturated or unsaturated heterocyclic ring containing 1to 3heteroatoms selected from nitrogen, sulfur, and oxygen includes as examples unsaturated members: pyridine, pyrrole, thiophene, or furan, and the like. Saturated members include, for example, piperidine, pyrrolidine, morpholine, thiomorpholine, imidazole, thiazole, oxazole, and the like. The preferred heterocyclic ring is morpholine.

The compounds of the Formulas I or II are capable of further forming pharmaceutically acceptable acid addition and/or base salts. All of these forms are within the scope of the present invention.

Pharmaceutically acceptable acid addition salts of the compounds of Formulas I or II include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono-and dicarboxylic acids, phenyl-substituted alkanoic acids, hydroxy alkanoic acids, alkanedioic acids, aromatic acids, aliphatic, and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, n-methyl glutamine [see, for example, Berge S. M., et al., "Pharmaceutical Salts," *Journal of Pharmaceutical Science* 66, 1–19 (1977)].

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with inorganic or organic bases, such as metal bases or amines, such as alkali and alkaline earth metal bases, e.g., hydroxides or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine [see, for example, Berge S. M., et al., "Pharmaceutical Salts," *Journal of Pharmaceutical Science* 66, 1–19 (1977)].

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

In determining when a cell adhesion inhibitor is indicated, of course inter alia, the particular condition in question and its severity, as well as the age, sex, weight, and the like of the subject to be treated, must be taken into consideration and this determination is within the skill of the attendant physician.

For medical use, the amount required of a compound of Formula I or II or pharmaceutically acceptable salt thereof to achieve a therapeutic effect will, of course, vary both with the particular compound, the route of administration, the mammal under treatment, and the particular disorder of disease concerned. A suitable dose of a compound of Formula I or pharmacologically acceptable salt thereof for a mammal suffering from, or likely to suffer from any condition as described hereinbefore is 0.1 $\mu$g to 500 mg of the compound per kilogram body weight. In the case of systemic administration, the dose may be in the range of 0.5 to 500 mg of the compound per kilogram body weight, the most preferred dosage being 0.5 to 50 mg/kg of mammal body weight administered two to three times daily. In the case of topical administration, e.g., to the skin or eye, a suitable dose may be in the range 0.1 ng to 100 $\mu$g of the compound per kilogram, typically about 0.1 $\mu$g/kg.

In the case of oral dosing for the treatment or prophylaxis of arthritis or inflammation in general, due to any course, a suitable dose of a compound of Formula I or II or pharmaceutically acceptable salt thereof, may be as specified in the preceding paragraph, but most preferably is from 1 mg to 10 mg of the compound per kilogram, the most preferred dosage being from 1 mg to 5 mg/kg of mammal body weight, for example, from 1 to 2 mg/kg.

It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferable to present it as a pharmaceutical formulation comprising a compound of Formula I or II or a pharmaceutically acceptable acid addition or base salt thereof and a pharmacologically acceptable carrier therefor. Such formulations constitute a further feature of the present invention.

The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intraarticular, topical, nasal, or buccal administration. Such formulations are understood to include long-acting formulations known in the art.

The formulations may conveniently be presented in unit dosage form and may be prepared by any of the methods well known in the art of pharmacy. All methods may include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets, or lozenges, each containing a predetermined amount of the active ingredient, in the form of a powder or granules, in the form of a solution or a suspension in an aqueous liquid or nonaqueous liquid, or in the form of an oil-in-water emulsion or a water-in-oil emulsion. The active ingredient may also be in the form of a bolus, electuary, or paste.

The usefulness of the compounds of the present invention as inhibitors of leukocyte adherence to vascular endothelium may be demonstrated by their effectiveness in various standard test procedures. A description of each procedure and exemplary test results follows.

Method for Determining the Inhibition of Human Neutrophil Adhesion to TNF-$\alpha$, IL-1$\alpha$, and LPS-Stimulated Human Umbilical Vein Endothelial Cells Isolation of Neutrophils Neutrophils were isolated from anticoagulant-treated venous blood obtained from healthy human volunteers according to the method of Ferrante and Thong [*J. Immunol. Methods* 24, 389-93 (1978)]. The cell preparations consisted of greater than 98% neutrophils.

Endothelial Cell Culture

Second passage human umbilical vein endothelial cells (HUVEC) (Clonetics, San Diego, Calif.) were seeded into Falcon 24-well cell culture plates (Becton Dickinson, Lincoln Park, N.J.) at approximately $2 \times 10^4$ cells per well. The cells were grown to confluent monolayers in endothelial basal medium (EBM, Clonetics) supplemented with 5% fetal calf serum (Hyclone Laboratories, Logan, Utah), 10 ng/mL EGF, 1 $\mu$g/mL hydrocortisone, 0.4% bovine brain extract (Clonetics) in 5% $CO_2$ at 37° C.

Neutrophil Adhesion

Neutrophils ($30 \times 10^6$) were labeled for 60 minutes at 37° C. with 100 $\mu$Ci $Na^{51}CrO_4$ (ICN Biomedicals, Costa Mesa, Calif.) in 2.0 mL $Ca^{2+}$- and $Mg^{2+}$-free Hanks' balanced salt solution (HBSS, GIBCO Laboratories, Grand Island, N.Y.). The cells were washed two times in HBSS and suspended in unsupplemented EBM.

Stimulation of HUVEC with tumor necrosis factor-$\alpha$ (TNF-$\alpha$) (Genzyme, Cambridge, Mass.), interleukin (IL-1$\alpha$) (Genzyme) or *E. coli* 0111: B4 lipopolysaccharide (LPS) (Sigma) in the presence or absence of drug was initiated 4 hours prior to the addition of neutrophils. The suspension medium was unsupplemented EBM or supplemented EBM for studies with cytokines or LPS, respectively. Such treatment has been shown to promote maximal expression of the endothelial cell-leukocyte adhesion molecule ELAM-1 as well as expression of ICAM-1 [*J. Immunol.* 137, 1893 (1986); *Proc. Natl. Acad. Sci. USA* 9238 (1987)]. Immediately prior to addition of $^{51}$Cr-labeled neutrophils to the HUVEC monolayers, the cultures were washed with 1 mL unsupplemented media to remove stimulus and/or drug. Neutrophils ($5 \times 10^5$) were then added to the HUVEC in 0.5 mL unsupplemented media and incubated at 37° C. for 30 minutes. Nonadherent neutrophils were removed by aspiration. Following an additional wash, adherent neutrophils were lysed with 0.5 mL 1N $NH_4OH$ overnight at 37° C. Lysates were collected and the radioactivity in each well was determined by gamma ray spectroscopy.

Modified Method for Determining the Inhibition of Human Neutrophil Adhesion to TNF-$\alpha$, IL-1$\alpha$, and LPS Stimulated Human Umbilical Vein Endothelial Cells The previous assay using $^{51}$Cr labeled human neutrophils has been modified. The neutrophils are now labeled with the fluorescent dye calcein. The current method allows for quantification of neutrophil adherence by fluorescence spectroscopy.

Cell Culture

Second passage HUVEC (Clonetics Corporation, San Diego, Calif., CC-2617) were seeded into Coring (Corning glass works, Corning, N.Y.) 96-well cell culture plates at approximately $5 \times 10^3$ cells/well and grown to confluency in supplemented endothelial basal medium (EBM, MCDB-131, Clonetics, 10 ng/mL EGF, 1 $\mu$g/mL hydrocortisone, 0.4% bovine brain extract, 5% Fetal Bovine Serum). One day prior to running the assay, typically 3 days postseeding, the cultures were refed with 0.2 mL/well supplemented EBM (S-EBM).

Preparation of Test Compounds

Test compounds were prepared as 10 mL stock solutions at a concentration of 1.0 mM. The compounds were initially solubilized in 0.1 mL DMSO followed by the addition of 9.9 mL S-EBM. The drug preparations were then diluted in one step to a concentration of 66.6 $\mu$M or 200 $\mu$M. Solubilizations and dilutions were performed in polystyrene containers.

Stimulation of HUVEC

Recombinant human tumor necrosis factor-$\alpha$ (TNF, Genzyme, Boston, Mass., code TNF-H) was prepared at 400 U/mL in S-EBM. Stock TNF was prepared to 20,000 U/mL in Delbecco's phosphate-buffered saline (PBS, Gibco, Grand Island N.Y.) plus 0.1% BSA and stored at −70° C. HUVEC were washed one time with 0.2 mL warm unsupplemented EBM and then stimulated for 4 hours at 37° C. with 200 U/mL TNF in the presence of 33.3 µM or 100 µM test compound. This was accomplished by adding 0.1 mL of 400 U/mL TNF and 0.1 mL 66.6 µM or 0.1 mL of 200 µM test compound. These additions were done slowly as to not disrupt the HUVEC monolayer. Each compound was tested in six wells. Unstimulated (vehicle control) and TNF-stimulated without test compound treatments were also run in each plate.

Labeling of Neutrophils

One hour prior to adding the neutrophils (isolated as previously described) to the HUVEC, neutrophils ($5 \times 10^6$/mL) were labeled for 30 minutes at 37° C. with 5 µM calcine-AM (Molecular Probes, Eugene, Oreg.) in Hanks' balanced salt solution plus 0.45% BSA. Stock calcein was prepared to 5mM in anhydrous DMSO and stored desiccated at −20° C. At the end of the incubation the cells were washed two times in cold HBSS and resuspended to a final concentration of $1 \times 10^6$ cells/mL in unsupplemented EBM.

Addition of Neutrophils to HUVEC

At the end of the 4-hour stimulation and immediately prior to the addition of the neutrophils to the HUVEC monolayer, the plates were washed with 0.2 ml warm unsupplemented EBM to remove TNF and drug. Neutrophils ($1 \times 10^5$ cells) were slowly added to each of the treated wells and incubated for 30 minutes at 37° C. At the end of the incubation the plates were washed two times with 0.2 mL warm unsupplemented EBM followed by a final addition of 0.1 mL for plate scanning.

Determination of Relative Fluorescence

The fluorescence was determined using a Millipore Cytofluor 2300 system (excitation=480, emission=530, sensitivity=4).

Calculations

The assay was considered valid if the TNF-stimulation of the HUVEC resulted in a 300% increase in neutrophil adherence over adherence to unstimulated HUVEC. Results were expressed as means of percent inhibition of TNF-stimulated adherence, using the following equation.

$$\% \text{ Inhibition} = 100 - \left( \frac{\text{stimulated adherence}_{(drug)} - \text{unstimulated adherence}}{\text{stimulated adherence}_{(control)} - \text{unstimulated adherence}} \right) \times 100$$

Certain compounds were tested at concentrations of 33.3 µM, 10.0 µM, 3.3 µM, and 1.0 µM to determine IC$_{50}$ values. Linear regression analysis of the means of the inhibition values were used to determine the IC$_{50}$.

The results obtained on the above testing of certain compounds of the present invention are shown in Tables 1 and 2.

TABLE 1

Inhibition of Adhesion by Compounds of Formula I

| Example | Adhesion ECA (% Inhibition or IC$_{50}$, µM) |
|---|---|
| 1 | 11.7[a] |
| 2 | 34%[b] |
| 3 | 32%[c] |
| 4 | 81%[b] |
| 5 | 48%[b] |
| 6 | 35%[c] |
| 7 | 19%[c] |
| 8 | 13%[c] |
| 9 | 15%[c] |
| 10 | 55%[c] |
| 11 | 27%[c] |
| 12 | 34%[c] |
| 13 | 21%[c] |
| 14 | 37%[c] |
| 15 | 7%[c] |
| 16 | 10%[c] |
| 17 | 24%[c] |
| 18 | 10%[c] |
| 19 | 30%[c] |
| 20 | 63%[c] |
| 21 | 53%[c] |
| 22 | 16%[d] |
| 23 | 7%[d] |
| 24 | 21%[d] |

[a]IC$_{50}$ µM
[b]% inhibition at 100 µM; neutrophils labeled with Cr.
[c]% inhibition at 33 µM; neutrophils labeled with calcein.
[d]% inhibition at 100 µM; neutrophils labeled with calcein.

TABLE 2

Inhibition of Adhesion by Compounds of Formula II

| Example | Adhesion ECA (% Inhibition or IC$_{50}$, µM) |
|---|---|
| 25 | 21%[c] |
| 26 | 24%[c] |
| 27 | 13[a] |
| 28 | 52%[d] |
| 29 | 20%[d] |
| 30 | 42%[d] |
| 31 | 11%[d] |
| 32 | 95%[d] |
| 33 | 15%[d] |
| 34 | 70%[d] |
| 35 | 61%[d] |
| 36 | 4%[d] |
| 37 | 68%[d] |
| 38 | 67%[c] |

[a]IC$_{50}$ µM
[c]% inhibition at 33 µM; neutrophils labeled with calcein.
[d]% inhibition at 100 µM; neutrophils labeled with calcein.

The compounds of the present invention have also been found to inhibit the activation of the human immunodeficiency virus (HIV), latent in infected mammals, and therefore are useful in the treatment of AIDS.

Attempts at understanding the virologic and cellular basis for the clinical asymptomatic period reveal that HIV exists as a dormant or nonexpressing provirus in a reservoir population of chronically infected cells. A specific type of HIV, HIV-1, has been the subject of a number of different research projects which have shown that the virus exists as a dormant or nonexpressing provirus in a reservoir population of chronically infected T-lymphocytic cells. Greater detail concerning the nuclear and biochemical mechanisms responsible for maintaining the nonexpressive viral state, however, is beyond the scope of this review, but can be found in detail elsewhere. "Mechanisms of HIV-1 Latency", Bednarik, et al., *AIDS* 1992; 6: 3–16.

Until recently, it was believed that HIV was dormant or nonexpressing in all the reservoir population of chronically infected cells during the clinical asymptomatic period. Observations of the low to absent levels of viraemia and virus replication in peripheral blood cells led to the impression that HIV disease was not active during the clinical asymptomatic period. A team of scientists, however, have discovered that a true state of microbiological latency does not exist during the course of HIV infection. Fauci A. S., et al., "HIV Infection is Active and Progressive in Lymphoid Tissue During the Clinically Latent Stage of disease", *Nature* 1993; 362: 355–358.

The scientists reported a dichotomy between the levels of viral burden and virus replication in peripheral blood versus lymphoid organs during clinical latency. Based on these findings, therefore, the scientists have discovered that "peripheral blood does not accurately reflect the actual state of HIV disease, particularly early in the clinical course of HIV infection. In fact, HIV disease is active and progressive even when there is little evidence of disease activity by readily measured viral parameters in the peripheral blood, and the patient is experiencing clinical latency."

Inevitably, the disease state of HIV progresses from the clinically latent asymptomatic period to the expressive and active symptomatic period. Through the use of several different models, an understanding of the cellular pathways involved in HIV activation from laboratory latency has begun to unfold. According to Butera, et al., *AIDS* 1992; 6: 994, many of the cellular models of latency can be induced to express HIV-1 upon treatment with cytokines. This indicates that in the state of microbiologic latency, HIV-1 awaits an extracellular stimulus before initiating replication. This signal not only can be mediated though a soluble cytokine interaction with its receptor, but also through receptor-receptor interactions which occur during cell to cell communication or cellular stress such as I/V light exposure and heat shock. Furthermore, an extracellular induction signal can be generated in an autocrine or paracrine fashion so that an HIV-1 activated cell can propagate its own expression while activating a nearby latent cell.

Additional factors have been considered by those of skill in the art to be involved in the activation of HIV. One study has shown that 12-O-tetradecanoylphorbol-13-acetate (TPA) mediates CD4 down regulation and viral expression in HIV-infected cells. Hamamoto, et al., *Biochem. Biophys. Res. Commun.* 1989; 164: 339–344. Interestingly, Hamamoto also examined the effect of the potent protein kinase C inhibitors staurosporine, H-7, and UCN-01 on TPA-mediated CD4 down regulation and augmentation of HIV expression. Staurosporine was found to be an effective TPA inhibitor for both of these actions.

The cellular pathways involved in mediating the activating signal from the plasma membrane to the integrated virus, resulting in HIV-1 expression, are much less clear. Recently, the development of a reliable and simple system for evaluating compounds that could prevent activation of latent HIV was reported at the National Cooperative Discovery Grant (NCDDG)/AIDS by P. Feorino, S. T. Butera, T. M. Folks, and R. F. Schinazi, San Diego, Calif., Nov. 3–7, 1991. The assay system employed the OM-10.1 cell line, a unique chronically-infected promyelocytic clone which remains CD4+ until HIV-1 activation with tumor necrosis factor-α. The expression of CD4+ on the cell surface and the activity of reverse transcriptase are used as markers for quantitating viral expression. Alternatively, other HIV markers, such as protease activity, which are known to those of skill in the art can be used. OM-10.1 cells remain CD4+ until viral activation and respond to tumor necrosis factor induction, and therefore, these cultures are used to conveniently and rapidly examine pharmacologics for an ability to prevent CD4+ down modulation (decrease in expression of CD4+ on the cell surface) and HIV-1 expression.

A variety of compounds known to have antiviral properties against either acutely or chronically infected cells were evaluated for their ability to inhibit HIV expression in these OM-10.1 cells. Several compounds that interact with biochemical pathways that may interfere with the reactivation process were also examined. The results of the evaluation were presented in a poster at the NCDDG/AIDS, San Diego, Calif., Nov. 3–7 (1991). Among some 48 compounds evaluated, 3'-fluoro-3'-deoxythymidine (FLT), interferon Y, and desferrioxamine were considered modest inhibitors of the activation of HIV-1.

A representative compound 5-methoxy-3-[(1-methylethyl)thio]benzo[b]thiophene-2-carboxamide showed an IC$_{50}$ of 0.4 μM inhibition in OM-10.1 cells.

The compounds of the present invention may be prepared by the following methods. As starting materials, 3-amino benzo[b]thiophene-2-carboxylate esters 1 are prepared by the known general method [Beck J. R., *J. Org. Chem.* 37, 3224 (1972)]. As depicted in Scheme 1, treatment of 1 with an alkyl nitrite and a copper II halide in acetonitrile at 0°–65° C. [Doyle M. P., et al., *J. Org. Chem.* 42, 2426 (1977)] gives the 3-halogen derivative 2. Reaction of 2 with an alkyl or aryl thiol in the presence of a base such as triethylamine in a solvent such as N,N'-dimethylformamide or acetonitrile at 0°–80° C. yields the thioether 4. Reductive amination of 1 with an aldehyde or ketone and sodium cyanoborohydride in acetic acid at 0°–80° C. gives the substituted amino esters of type 3a. Preparation of compounds of type 3b is possible by alkylation of 1 with an alkyl halide in the presence of a base such as sodium bicarbonate in a polar solvent such as N,N'-dimethylformamide or 1,3-dimethyl-2-imidazolidinone. Compounds of type 3b can be further treated to give compounds of type 3c. Compounds of type 3c (where R$_7$=R$_2$) can also be obtained directly from 1 by using excess amounts of reagents.

SCHEME 1

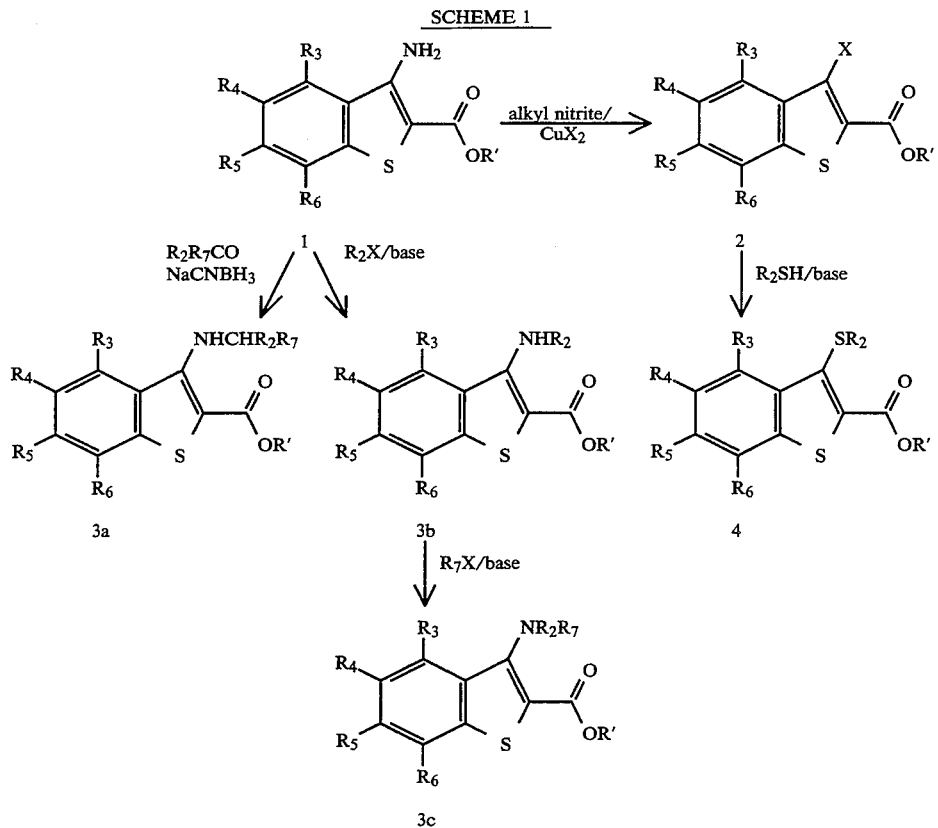

Saponification of the 3-sulfur or 3-nitrogen substituted benzo[b]thiophene esters 5 with a base such as sodium hydroxide or potassium hydroxide in water or an alcohol water mixture yields the carboxylic acids 6 (Scheme 2). Reaction of 6 with a coupling agent, preferably 1,1′-carbonyldiimidazole (CDI), in a solvent such as tetrahydrofuran or acetonitrile to form the corresponding imidazolide or other leaving group and subsequent addition of aqueous ammonium hydroxide or ammonia gives the desired primary benzo[b]thiophene-2-carboxamides 7. Alternatively, the benzo[b]thiophene-2-carboxylic acids are converted to the acid halide via a reagent such as thionyl chloride, or preferably oxalyl chloride with a catalytic amount of dimethylformamide in a solvent such as methylene chloride or tetrahydrofuran. Subsequent reaction with aqueous ammonium hydroxide or ammonia gives the desired primary benzo[b]thiophene-2-carboxamides. The primary amides 7 can also be prepared by treatment of the corresponding benzo[b]thiophene-2-carboxylic acid esters with lithium amide in liquid ammonia in the presence of a co-solvent such as tetrahydrofuran at temperatures of −78° C. to 25° C.

A similar procedure is used to prepare the secondary benzo[b]thiophene-2-carboxamides, 8. Instead of aqueous ammonium hydroxide, the intermediate imidazolide or acid chloride is reacted with a primary amine in the presence or absence of a base such as triethylamine or 1,8-diazabicyclo[5.4.0]undec-7-ene (DBU). When the amine is in the form of its HCl salt additional base is required to obtain the free amine.

SCHEME 2

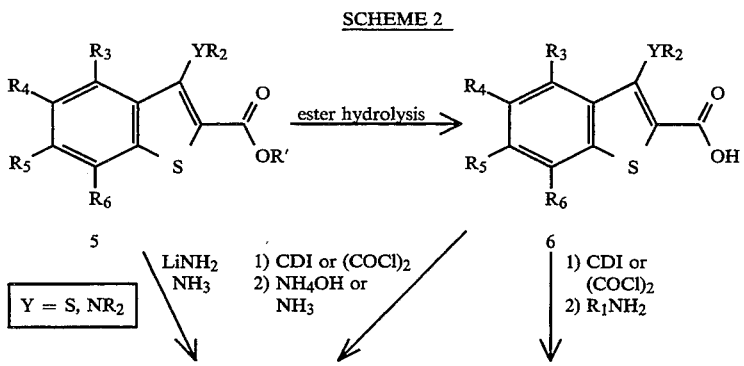

SCHEME 2

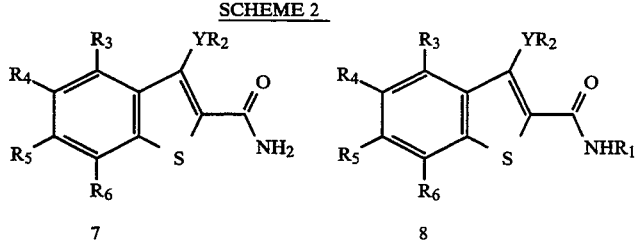

An alternate route to 3-thiobenzo[b]thiophene-2-carboxamides is depicted in Scheme 3. Addition of an amine to 3-chlorobenzo[b]thiophene-2-carbonyl chlorides of type 9 provides 3-chlorobenzo[b]thiophene-2-carboxamides of type 10. Compounds of type 9 are prepared as documented [Connor D. T., et al., *J. Med. Chem.* 35, 958 (1992)]. Treatment of 10 with thioacetamide in the presence of a base such as 1,8-diazabicyclo[5.4.0]undec-7-ene (DBU) and a solvent such as N,N-dimethylformamide or tetrahydrofuran gives 3-thiol compounds of structure 11. Alkylation of 11 with an alkyl or aryl halide with a base such as sodium bicarbonate or 1,8-diazabicyclo[5.4.0]undec-7-ene (DBU) in a solvent such as tetrahydrofuran provides compounds of structure 12. Compounds of this type can also be obtained from compounds of type 10 via reaction with a primary thiol derivative in the presence of base such as 1,8-diazabicyclo[5.4.0]undec-7-ene (DBU) in a solvent such as tetrahydrofuran or N,N-dimethylformamide. Alternatively, compounds of type 10 are treated with the sodium or other metal salt of a thiol in a polar solvent such as N,N-dimethylformamide. Oxidation of 12 with an oxidizing agent such as m-chloroperbenzoic acid or sodium perborate provides compounds of type 13, where n is an integer of 1 or 2.

SCHEME 3

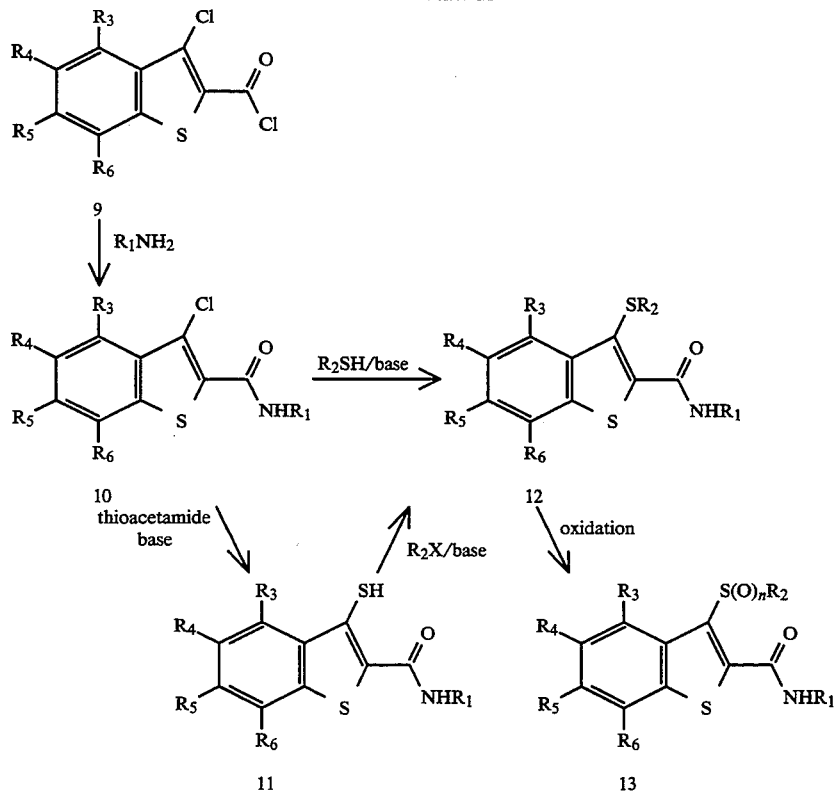

Scheme 4 shows the preparation of secondary benzo[b]thiophene-2-carboxamides of type 15, that contain a carboxylic acid substituent on the amide functionality. These compounds are prepared via an intermediate ester. As in Scheme 2 the benzo[b]thiophene-2-carboxylic acid 6 is activated and then treated with an amine that contains the desired ester residue. The amine can be in the form of its HCl salt. The intermediate, 14, is isolated and the ester functionality is hydrolyzed, preferably with sodium hydroxide in aqueous ethanol, to give the desired carboxylic acid, 15.

SCHEME 4

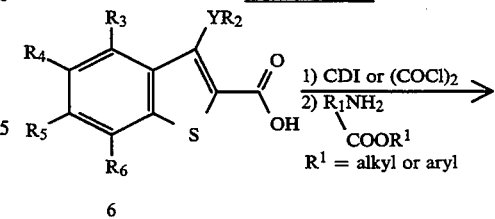

19

-continued
SCHEME 4

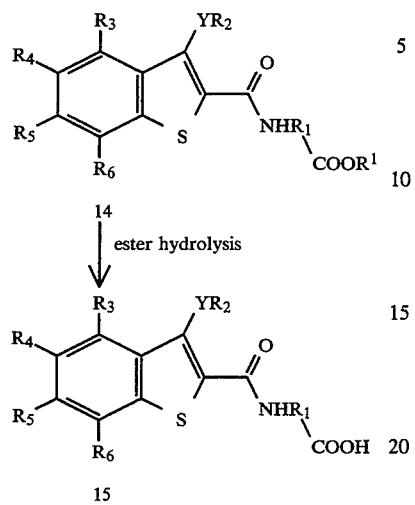

Compounds such as 17, that contain a carboxylic acid substituent at C-3, can also be prepared via an ester

20

-continued
SCHEME 5

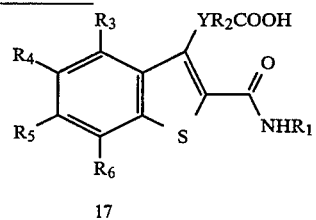

Scheme 6 depicts the preparation of benzo[b]thiophene-2-carboxamide-1-oxides. The starting materials, 18, are prepared as documented [Boschelli D. H., et al., U.S. Pat. No. 5,208,253, (1993)]. Formation of the sodium salt with sodium hydride followed by addition of thionyl chloride and a controlled amount of an amine provides compounds of type 19. In those cases where an excess amount of amine is used, compounds of structure 20 are obtained. Treatment of compounds of type 19 with an amine gives compounds of type 21. Compounds of type 22 are obtained by reaction of 19 with thiols. Alternatively, compounds of type 21 can be obtained by oxidation of compounds of type 8 where Y=NR$_2$.

SCHEME 6

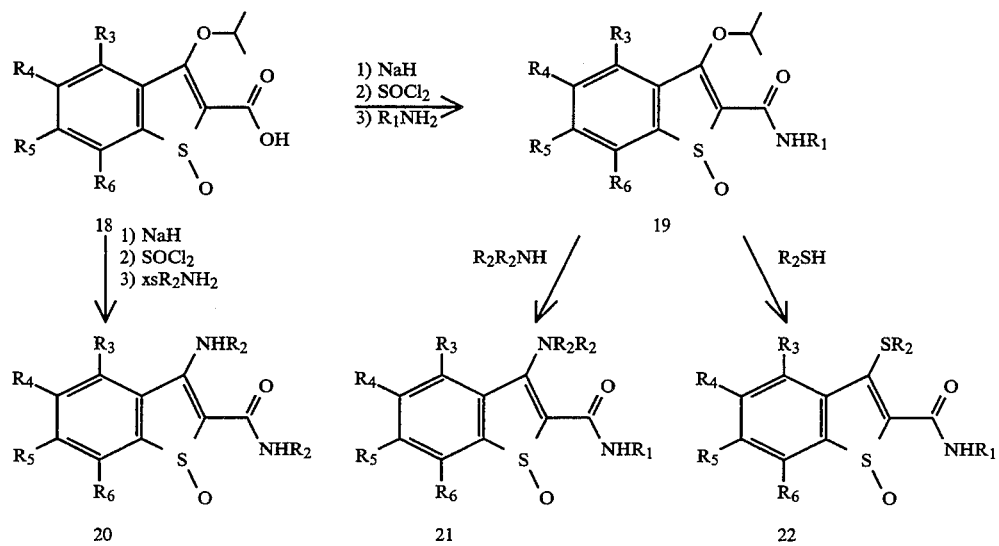

intermediate, 16. As shown in Scheme 5, intermediate 16 can be isolated, then hydrolyzed, preferably with sodium hydroxide in aqueous ethanol, to give the desired carboxylic acid.

SCHEME 5

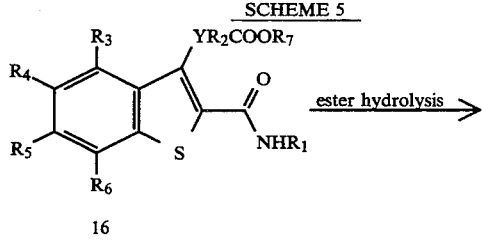

Those compounds where one or more of R$_3$-R$_6$ is hydroxy are prepared via an intermediate that has a suitable hydroxy protecting group. As an example, Scheme 7 shows the preparation of 5-hydroxy-benzo[b]thiophene-2-carboxamides. The amides are prepared from the corresponding acid containing a hydroxy group protected as its benzyl ether. The benzyl group is then removed, preferably by hydrogenation. Other protecting groups, such as silyl groups, can also be used and later removed using standard methodology.

SCHEME 7

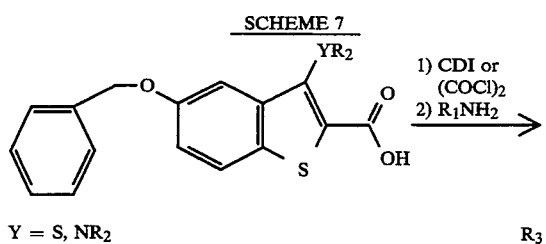

Y = S, NR₂

SCHEME 8

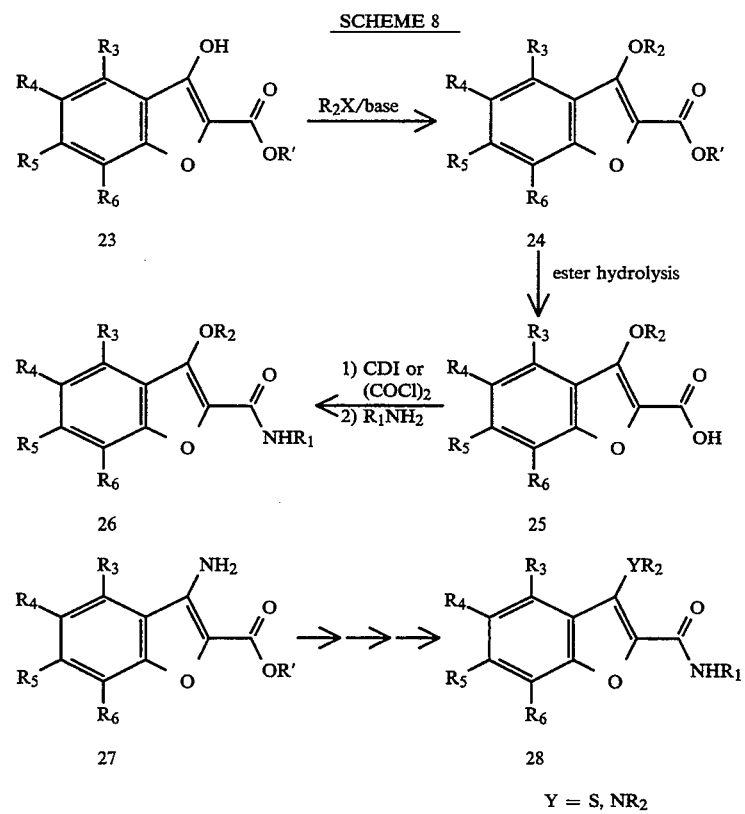

Y = S, NR₂

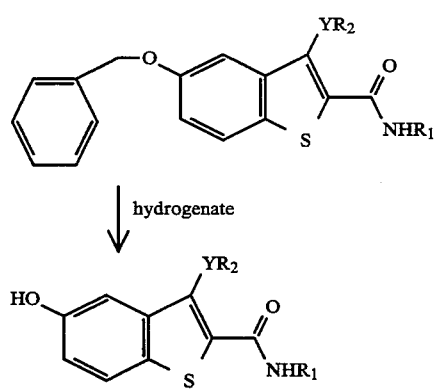

Benzofuran starting materials (Scheme 8) are prepared by well known methods as described for example in Cagniant P., Cagniant D., *Advances in Heterocyclic Chemistry* 18, 337 (1975). The 3-hydroxybenzofuran esters, 23, are treated with an alkyl or aryl halide or an alkyl sulfate in the presence of a base such as potassium t-butoxide or DBU in acetone, acetonitrile, or dimethyl- sulfoxide at 0°–80° C. to provide esters of type 24. These esters are converted to the corresponding benzofuran carboxylic acids, 25, and amides, 26, as described previously for the benzothiophenes. The 3-aminobenzofurans, 27, are prepared by the procedures described by [Beck J. R., Suhr R. G., *J. Hetero. Chem.* 11(2) , 227 (1974) , and Sangapure S. S., Agasimundin Y. S., *Indian J. Chem.* 14B (9) , 688 (1976)]. The conditions noted in the previous schemes can be used to convert compounds of type 27 into the desired derivatives 28.

Conditions within the description of Schemes 1 through 8 and variations in the description are known or can readily be determined from analogous reactions known to one skilled in the art.

The following examples are illustrative of the preparation of the compounds of the present invention.

EXAMPLES

Preparative Example 1

3-Chloro-5-methoxybenzo[b]thiophene-2-carboxamide

To a suspension of 3-chloro-5-methoxybenzo[b]thiophene-2-carbonyl chloride (1.52 g, 5.82 mmol) [Connor D. T., et al., *J. Med. Chem.* 35, 935 (1992)] in 80 mL of toluene at 50° C. is added dropwise 10 mL of aqueous NH₄OH. The resulting precipitate is collected by filtration and recrystallized from methanol to provide 3-chloro-5-methoxybenzo[b]thiophene2-carboxamide; mp=220°–222° C.

Example 1

5-Methoxy-3-[(1-methylethyl)thio]benzo[b]thiophene-2-carboxamide

2-Propanethiol (1.1 mL, 12.4 mmol) is added to a suspension of 3-chloro-5-methoxybenzo[b]thiophene-2-carboxamide (3.00 g, 12.4 mmol) in 24 mL of DMF. Diazabicycloundecene (DBU) (1.8 mL, 12.4 mmol) is added and the mixture is warmed to 80° C. After 6 hours, additional amounts of 2-propanethiol (110 μL) and of DBU (180 μL) are added. Heating is continued for 1 hour. The reaction mixture is allowed to cool and then is diluted with ethyl acetate and washed with 1N NaOH, 1N HCl, water, and brine. The organic layer is dried over MgSO4. Filtration followed by concentration in vacuo and recrystallization from ethyl acetate:-hexane gives 5-methoxy-3-[(1-methylethyl)thio]benzo[b]thiophene-2-carboxamide in 80% yield. An analytical sample is obtained by a second recrystallization from ethyl acetate:hexane; mp=143°–143.5° C.

Example 2

3-[(1-Methylethyl)thio]benzo[b]thiophene-2-carboxamide

To 3-[(1-methylethyl)thio]benzo[b]thiophene-2-carboxylic acid (133 mg, 0.53 mmol) [Connor D. T., et al., U.S. Pat. No. 4,703,053 (1987)] in 6 mL of THF is added N,N-carbonyldiimidazole (99 mg, 0.61 mmol). The mixture is heated at reflux for 1.5 hours then cooled slightly. Aqueous NH4OH (1 mL) is added and the reaction mixture is stirred at room temperature for 30 minutes, then partitioned between ethyl acetate and brine. The organic layer is dried over MgSO4, filtered, and concentrated in vacuo. The crude product is purified by flash chromatography eluting with 1:1 hexane:ethyl acetate to provide 3-[(1-methylethyl)thio]benzo[b]thiophene-2-carboxamide in 83% yield; mp=183–185° C.

Example 3

5-Methoxy-3-[(1-methylethyl)sulfonyl]benzo[b]thiophene-2-carboxamide

5-Methoxy-3-[(1-methylethyl)thio]benzo[b]thiophene-2-carboxamide (150 mg, 0.53mmol) is dissolved in 10 mL of dichloromethane. The solution is cooled to 0° C. and mCPBA (162 mg, 1.17 mmol) is added. The reaction mixture is allowed to warm to room temperature and stirred for 4 hours. The mixture is then cooled to 0° C. and additional mCPBA (32 mg) is added. The ice bath is removed and stirring is continued for 1 hour. The reaction mixture is partitioned between ethyl acetate and saturated NaHCO3. The organic layer is washed an additional 3 times with saturated NaHCO3, followed by water and brine. The organic layer is dried over MgSO4, filtered, and concentrated in vacuo. Recrystallization from ethyl acetate:hexane provides 5-methoxy-3-[(1-methylethyl)sulfonyl]benzo[b]thiophene-2-carboxamide in 53% yield; mp=169°–170° C.

Example 4

5-Methoxy-3-(methylthio)benzo[b]thiophene-2-carboxamide

Sodium thiomethoxide (93 mg, 1.32 mmol) is added to a suspension of 3-chloro-5-methoxybenzo[b]thiophene-2-carboxamide (250 mg, 1.03 mmol) in 2 mL of DMF. After 1 hour, an additional amount of sodium thiomethoxide (13 mg) is added. The reaction mixture is diluted with ethyl acetate and washed with 1N NaOH, 1N HCl, water, and brine. The organic layer is dried over MgSO4. Filtration followed by concentration in vacuo and recrystallization from ethyl acetate:hexane gives 5-methoxy-3-(methylthio)benzo[b]thiophene-2-carboxamide in 72% yield; mp=171°–173° C.

Example 5

5-Methoxy-3-(phenylthio)benzo[b]thiophene-2-carboxamide

Thiophenol (116 μL, 1.13 mmol) is added to a suspension of 3-chloro-5-methoxybenzo[b]thiophene-2-carboxamide (250 mg, 1.03 mmol) in 2 mL of DMF. Diazabicycloundecene (DBU) (169 μL, 1.13 mmol) is added and the mixture is warmed to 80° C. After 2 hours, the reaction mixture is allowed to cool and is diluted with ethyl acetate and washed with 1N NaOH, 1N HCl, water, and brine. The organic layer is dried over MgSO4. Filtration followed by concentration in vacuo and recrystallization from ethyl acetate:hexane gives 5-methoxy-3-(phenylthio)benzo[b]thiophene-2-carboxamide in 84% yield; mp 194°–196° C.

Example 6

5-Methoxy-3-[(phenylmethyl)thio]benzo[b]thiophene-2-carboxamide

Benzylmercaptan (134 μL, 1.14 mmol) is added to a suspension of 3-chloro-5-methoxybenzo[b]thiophene-2-carboxamide (250 mg, 1.03 mmol) in 2 mL of DMF. Diazabicycloundecene (DBU) (170 μL, 1.14 mmol) is added and the mixture is warmed to 50° C. After 1 hour, the reaction mixture is allowed to cool and then is diluted with ethyl acetate and washed with 1N NaOH, 1N HCl, water, and brine. The organic layer is dried over MgSO4. Filtration followed by concentration in vacuo and recrystallization from ethyl acetate: hexane gives 5-methoxy-3-[(phenylmethyl)thio]benzo[b]thiophene-2-carboxamide in 63% yield; mp=151°–153° C.

Preparative Example 2

Methyl 4-[[[3-chloro-5-methoxybenzo[b]thien-2-yl]carbonyl]amino]benzoate

To a 0° C. solution of 3-chloro-5-methoxybenzo[b]thiophene-2-carbonyl chloride (500 mg, 1.9 mmol) in 20 mL of THF is added methyl p-aminobenzoate (318 mg, 2.1 mmol) followed by triethylamine (293 μL, 2.1 mmol). The reaction mixture is allowed to warm to room temperature and stirring is continued overnight. The mixture is partitioned between ethyl acetate and 1N HCl, then washed with 1N NaOH, saturated NaHCO3, and brine. The organic layer is dried over MgSO4. Filtration followed by concentration in vacuo and recrystallization from ethyl acetate:hexane provides 225 mg of methyl 4-[[[3-chloro-5-methoxybenzo[b]thien-2-yl]carbonyl]amino]benzoate; mp=205°–206° C.

Example 7

Methyl 4-[[[5-methoxy-3-[(1-methylethyl)thio]benzo[b]thien-2-yl]carbonyl]amino]benzoate 2-Propanethiol (32 μL, 0.35 mmol) is added to a solution of methyl 4-[[[3-chloro-5-methoxybenzo[b]thien-2-yl]carbonyl]amino]benzoate (100 mg, 0.27 mmol) in 1 mL of DMF. Diazabicycloundecene (DBU) (52 μL, 0.35 mmol) is added and the mixture is stirred at room temperature for 5 hours. The reaction mixture is diluted with ethyl acetate and washed with 1N HCl, water, and brine. The organic layer is dried over MgSO4. Filtration followed by concentration in vacuo and recrystallization from ethyl acetate:hexane gives methyl 4-[[[5-methoxy-3-[(1-methylethyl)thio]benzo[b]thien-2-yl]carbonyl]amino]benzoate in 72% yield; mp=157.5°–158.5° C.

Example 8

4-[[[5-Methoxy-3[(1-methylethyl)thio]benzo[b]thien-2yl]carbonyl]amino]benzoic acid A suspension of lithium hydroxide-monohydrate (20 mg, 0.48 mmol) and methyl 4-[[[5-methoxy-3-[(1-methylethyl)thio]benzo[b]thien-2yl]carbonyl]amino]benzoate (67 mg, 0.16 mmol) in 4 mL of methanol and 2 mL of water is heated at reflux for 1.5 hours. The reaction mixture is cooled to room temperature and then diluted with ethyl acetate and washed sequentially with 1N HCl, water, and brine. The organic layer is dried over MgSO$_4$. Filtration followed by concentration in vacuo and recrystallization from ethyl acetate: hexane gives 4-[[[5-methoxy-3-[(1-methylethyl)thio]benzo[b]thien-2yl]carbonyl]amino]benzoic acid in 78% yield; mp=241°–245° C. dec.

Example 9

3-Mercapto-5-methoxybenzo[b]thiophene-2-carboxamide

Diazabicycloundecene (DBU) (1.8 mL, 12.3 mmol) is added to a room temperature solution of 3-chloro-5-methoxybenzo[b]thiophene-2-carboxamide (1.0 g, 4.1 mmol) and thioacetamide (1.0 g, 13.1 mmol) in 10 mL of DMF. The mixture is warmed to 80° C. for 5.5 hours. The reaction mixture is allowed to cool and is diluted with ethyl acetate and washed with 1N HCl and water. The organic layer is extracted four times with 1N NaOH followed by water. The basic layers are combined and acidified with 6N HCl. The precipitate is filtered and washed with water. Recrystallization from ethyl acetate:hexane gives 3-mercapto-5-methoxybenzo[b]thiophene-2-carboxamide in 71% yield; mp=205° C. dec.

Example 10

Methyl 3-[[2-(aminocarbonyl)-5-methoxybenzo[b]thien-3-yl]thio]propanoate

Methyl bromopropionate (75 μL, 0.69 mmol) is added to a room temperature solution of 3-mercapto-5-methoxybenzo[b]thiophene-2-carboxamide (150 mg, 0.63 mmol) in 7 mL of THF followed by NaHCO$_3$ (334 mg, 3.15 mmol). Additional methyl bromopropionate (150 μL) and Na$_2$CO$_3$ (70 mg) are added and the reaction mixture is stirred at room temperature overnight. The reaction mixture is diluted with ethyl acetate and washed with 1N HCl, water, 1N NaOH, water, and brine. The organic layer is dried over MgSO$_4$. Filtration followed by concentration in vacuo and recrystallization from ethyl acetate: hexane followed by recrystallization from methanol: water gives methyl 3-[[2-(aminocarbonyl)-5-methoxybenzo[b]thien-3-yl]thio]propanoate in 46% yield; mp=142°–144° C.

Example 11

5-Methoxy-3-[[2-(4-morpholinyl)ethyl]thio]benzo[b]thiophene-2-carboxamide

Diazabicycloundecene (DBU) (990 μL, 6.62 mmol) is added to a suspension of 3-chloro-5-methoxybenzo[b]thiophene-2-carboxamide (200 mg, 0.83 mmol) and 4-morpholineethanethiol hydrochloride (608 mg, 3.31 mmol) in 4 mL of DMF. The mixture is stirred at room temperature for 3 hours then diluted with ethyl acetate and washed with water followed by aqueous citric acid. NaHCO$_3$ is added to the acidic extracts and the precipitated solids are collected and washed with water. Recrystallization from methanol:water provides 5-methoxy-3-[[2-(4-morpholinyl)ethyl]thio]benzo[b]thiophene-2-carboxamide in 83% yield; mp=158.5°–159.5° C.

Preparative Example 3

Methyl 3-bromo-4-chlorobenzo[b]thiophene-2-carboxylate

A mixture of copper (II) bromide (4.9 g, 22 mmol) and tert-butyl nitrite (3.3 mL, 2.9 g, 28 mmol) in 70 mL of acetonitrile is cooled in ice while methyl 3-amino-4-chlorobenzo[b]thiophene-2-carboxylate (4.4 g, 18 mmol) [Beck J. R., supra] is added in small portions. The cooling bath is removed and the mixture is stirred at room temperature for 24 hours, then added to 350 mL of cold 4.0N HCl. The precipitated solid is filtered, washed with water, and recrystallized from aqueous 2-propanol to yield 2.3 g (41%) of product; mp=120°–122° C.

4-Chloro-3-[(1-methylethyl)thio]benzo[b]thiophene-2-carboxylic acid

A mixture of methyl 3-bromo-4-chlorobenzo[b]thiophene-2-carboxylate (0.62 g, 2.0 mmol), 2-propanethiol (0.30 mL, 0.25 g, 3.2 mmol), and 1,8-diazabicyclo[5.4.0]undec-7-ene (0.33 mL, 0.34 g, 2.2 mmol) in 5.0 mL of N,N-dimethylformamide is stirred at room temperature for 24 hours. The reaction mixture is partitioned between 150 mL of cold 1.0N HCl and 75 mL of dichloromethane, and the aqueous layer is extracted several times with fresh dichloromethane. The combined organic layers are washed with 1.0N HCl and brine, then dried (anhydrous sodium sulfate) and evaporated to yield methyl 4-chloro-3-[(1-methylethyl)thio]benzo[b]thiophene-2-carboxylate as an oil.

The above oil is dissolved in 5.0 mL of methanol and 10.0 mL of 1.0N aqueous sodium hydroxide is added. The mixture is stirred at reflux for 4 hours, then cooled and added to 50 g of ice and water. The mixture is washed with ether (discarded), and the aqueous layer is cooled in ice and acidified with concentrated HCl. The precipitated solid is filtered and washed with water to yield 0.44 g (76%) of product acid, suitable for further reaction; mp=107°–109° C.

Example 12

4-Chloro-3-[(1-methylethyl)thio]benzo[b]thiophene-2-carboxamide

A mixture of 4-chloro-3-[(1-methylethyl)thio]benzo[b]thiophene-2-carboxylic acid (0.43 g, 1.5 mmol) and 1,1'-carbonyldiimidazole (0.25 g, 1.5 mmol) in 5.0 mL of acetonitrile is stirred at reflux for 2 hours. The cooled reaction solution is added slowly to 20 mL of cold ammonium hydroxide solution. The precipitated solid is filtered, washed with water, and recrystallized from aqueous acetonitrile to give 0.15 g (35%) of product; mp=182°–184° C.

Example 13

Methyl 3-[[2-(aminocarbonyl)-5-methoxybenzo[b]thien-3-yl]thio]pentanoate

Methyl 5-bromovalerate (144 μL, 1.00 mmol) is added to a room temperature solution of 3-mercapto-5-methoxybenzo[b]thiophene-2-carboxamide (200 mg, 0.84 mmol) in 8 mL of THF followed by NaHCO$_3$ (351 mg, 4.18 mmol) and the reaction mixture is stirred at room temperature overnight. Additional methyl 5-bromovalerate (100 μL) is added and the reaction mixture is stirred at room temperature for 3 days. The reaction mixture is diluted with ethyl acetate and washed with 1N HCl, water, saturated NaHCO$_3$, and brine. The organic layer is dried over MgSO$_4$. Filtration followed by concentration in vacuo and recrystallization from ethyl acetate:hexane gives methyl 3-[[2-(aminocarbonyl)-5-methoxybenzo[b]thien-3-yl]thio]pentanoate in 30% yield; mp=134.5°-135.5° C.

Example 14

5-[[2-Aminocarbonyl)-5-methoxybenzo[b]thien-3-yl]thio]pentanoic acid

A mixture of methyl 3-[[2-(aminocarbonyl)-5-methoxybenzo[b]thien-3-yl]thio]pentanoate (150 mg, 0.42 mmol) and lithium hydroxide monohydrate (18 mg, 0.42 mmol) in 2 mL of water and 2 mL of methanol is heated at reflux for 6.5 hours during which time additional lithium hydroxide monohydrate (5 mg) is added. The reaction mixture is cooled, diluted with ethyl acetate, and washed with 1N HCl, water, and brine. The organic layer is dried over MgSO$_4$. Filtration followed by concentration in vacuo and recrystallization from ethyl acetate:hexane gives 5-[[2-(aminocarbonyl-5-methoxybenzo[b]thien-3-yl]thio]pentanoic acid in 88% yield; mp=171.5°-172° C.

Example 15

[[2-(Aminocarbonyl)-5-methoxybenzo[b]thien-3-yl]thio]acetic acid

Bromoacetic acid (72 mg, 0.52 mmol) is added to a room temperature solution of 3-mercapto-5-methoxybenzo[b]thiophene-2-carboxamide (50 mg, 0.21 mmol) in 3 mL of THF followed by NaHCO$_3$ (219 mg, 2.60 mmol) and the reaction mixture is stirred at room temperature for 4 hours. The reaction mixture is diluted with ethyl acetate and washed with 1N HCl and brine. The organic layer is dried over MgSO$_4$. Filtration followed by concentration in vacuo and recrystallization from ethyl acetate:hexane provides [[2-(aminocarbonyl)-5-methoxybenzo[b]thien-3-yl]thio]acetic acid in 54% yield; mp=126°-127° C.

Example 16

Methyl 4-[[[2-(aminocarbonyl)-5-methoxybenzo[b]thien-3-yl]thio]methyl]benzoate Methyl 4-(bromomethyl)benzoate (479 mg, 2.09 mmol) is added to a room temperature solution of 3-mercapto-5-methoxybenzo[b]thiophene-2-carboxamide (200 mg, 0.84 mmol) in 12 mL of THF followed by NaHCO$_3$ (351 mg, 4.18 mmol) and the reaction mixture is stirred at room temperature overnight. The reaction mixture is diluted with ethyl acetate and washed with 1N HCl, saturated NaHCO$_3$, and brine. The organic layer is dried over MgSO$_4$, filtered, and concentrated in vacuo. Chromatography eluting with ethyl acetate:dichloromethane (1:9 to 1:1) followed by recrystallization from ethyl acetate:hexane provides methyl 4-[[[2-(aminocarbonyl)-5-methoxybenzo[b]thien-3-yl]thio]methyl]-benzoate in 68% yield; mp=150°-152° C.

Preparative Example 4

3-Chloro-5-(phenylmethoxy)benzo[b]thiophene-2-carboxamide

To a warm solution of 3-chloro-5-(phenylmethoxy)-benzo[b]thiophene-2-carbonyl chloride (2.0 g, 6 mmol) [Connor D. T., et al., *J. Med. Chem*, 35, 935, (1992)] in 20 mL of toluene is added dropwise 10 mL of aqueous NH$_4$OH. The resulting precipitate is collected by filtration washing with ethyl alcohol to provide 3-chloro-5-(phenylmethoxy)benzo[b]thiophene-2-carboxamide in 84% yield; mp=205.5°-206° C.

Example 17

3-[(1-Methylethyl)thio]-5-(phenylmethoxy)benzo[b]thiophene-2-carboxamide

2-Propanethiol (0.8 mL, 8 mmol) is added to a solution of 3-chloro-5-(phenylmethoxy)benzo[b]thiophene-2-carboxamide (1.0 g, 3 mmol) and diazabicycloundecene (DBU) (2.6 mL, 17 mmol) in 10 mL of DMF and the mixture is warmed to 55° C. for 1 hour. The reaction mixture is allowed to cool and then poured into water and stirred. After 1 hour, the precipitate is filtered off, washed with water, and dried to provide 3-[(1-methylethyl)thio]-5-(phenylmethoxy)benzo[b]thiophene-2-carboxamide in 98% yield; mp=150°-152° C.

Preparative Example 5

4-Chloro-3-(dimethylamino)benzo[b]thiophene-2-carboxylic acid

A mixture of methyl 3-amino-4-chlorobenzo[b]thiophene-2-carboxylate (1.7 g, 7.0 mmol) [Beck J. R., supra] and paraformaldehyde (2.0 g, 67 mmol) in 45 mL of acetic acid is treated in portions with sodium cyanoborohydride (2.0 g, 32 mmol). The mixture is stirred at room temperature for 24 hours, then diluted cautiously with 250 g of ice and water. Solid sodium carbonate is added until the mixture is slightly basic. After extraction with ethyl acetate, the combined organic layers are washed with brine, then dried (anhydrous sodium sulfate), and evaporated to provide methyl 4-chloro-3-(dimethylamino)benzo[b]thiophene-2-carboxylate as an oil.

The above oil is dissolved in 20 mL of methanol. A solution of sodium hydroxide (0.60 g, 15 mmol) in 10 mL of water is added, and the mixture is stirred at reflux for 2 hours. The cooled reaction mixture is condensed under vacuum to one-third of the original volume, and the residue is added to 100 g of ice and water. The solution is acidified with 2.0 mL of acetic acid, and the precipitated solid is filtered and washed with water. Recrystallization from aqueous acetonitrile gives 0.97 g (54%) of product; mp=145° C. dec.

Example 18

4-Chloro-3-(dimethylamino)benzo[b]thiophene-2-carboxamide

Prepared from 4-chloro-3-(dimethylamino)benzo[b]thiophene-2-carboxylic acid by the procedure of Example 12. Yield 25% after recrystallization from ethyl acetate:hexane; mp=194°-196° C.

Example 19

3-Amino-4-methoxybenzo[b]thiophene-2-carboxamide

Lithium amide in liquid ammonia is prepared as described by Unangst P. C., Carethers M. E., *J. Heterocyclic. Chem.* 21, 709 (1984), from lithium metal ribbon (0.16 g, 23 mmol). A solution of methyl 3-amino-4-methoxybenzo[b]thiophene-2-carboxylate (1.3 g, 5.5 mmol) [Beck J. R., supra] in 10 mL of tetrahydrofuran is added dropwise. The mixture is stirred for 18 hours as the excess ammonia is permitted to evaporate. The residue is treated with 250 g of ice and water. The solid product is filtered, washed with water, and recrystallized from aqueous ethanol to yield 0.70 g (58%) of product; mp=151°-153° C.

Example 20

3-(Dimethylamino)-4-methoxybenzo[b]thiophene-2carboxamide

Alkylation of methyl 3-amino-4-methoxybenzo[b]thiophene-2-carboxylate (1.4 g, 5.9 mmol) [Beck J. R., supra] with paraformaldehyde as described for the preparation of methyl 4-chloro-3-(dimethylamino)benzo[b]thiophene-2-carboxylate provides methyl 3-(dimethylamino)-4-methoxybenzo[b]thiophene-2-carboxylate as a crude solid suitable for further synthesis; mp=69°-73° C.

The above solid (1.5 g, 5.7 mmol) is reacted with lithium amide as described in Example 19 to give 0.46 g (32%) of amide product after recrystallization from ethyl acetate:hexane; mp=219°-221° C.

Preparative Example 6

5-(Methylthio)-2-nitrobenzonitrile

A solution of 5-chloro-2-nitrobenzonitrile (10.0 g, 55 mmol) in 150 mL of N,N-dimethylformamide is cooled in ice and treated dropwise with a solution of sodium sulfide nonahydrate (15.8 g, 66 mmol) in 45 mL of water. The mixture is stirred for 15 minutes and then iodomethane (4.0 mL, 9.1 g, 64 mmol) is added dropwise. The ice bath is removed and the mixture is stirred at room temperature for 3 hours, then added to cold water. The precipitated solid is filtered and washed with water to give 9.2 g (87%) of product suitable for further synthesis; mp=107°-108° C. Methyl 3-amino-5-(methylthio)benzo[b]thiophene-2-carboxylate A solution of 5-methylthio-2-nitrobenzonitrile (1.0 g, 5.2 mmol) and methyl thioglycolate (1.1 mL, 1.3 g, 12.3 mmol) in 10 mL of N,N-dimethylformamide is cooled in ice and treated in portions with lithium hydroxide monohydrate (0.50 g, 11.9 mmol). The cooling bath is removed and the mixture is stirred at room temperature for 16 hours, then added to cold water. The precipitated solid is filtered, washed with water, and recrystallized from ethyl acetate:hexane to yield 0.78 g (60%) of product; mp=112°-113° C.

Methyl 3-dimethylamino-5-(methylthio)benzo[b]thiophene-2-carboxylate

Prepared from methyl 3-amino-5-(methylthio)-benzo[b]thiophene-2-carboxylate by alkylation with formaldehyde as described in the preparation of methyl 4-chloro-3-(dimethylamino)benzo[b]thiophene-2-carboxylate. Yield 71% after recrystallization from ether-petroleum ether; mp=63°-66° C.

Example 21

3-Dimethylamino-5-(methylthio)benzo[b]thiophene-2-carboxamide

Prepared from methyl 3-dimethylamino-5-(methylthio)benzo[b]thiophene-2-carboxylate by reaction with lithium amide as described in Example 19. Purification of the crude product by flash chromatography (silica gel, elution with 30% ethyl acetate in hexane) gives 64% of product; mp=140°-142° C.

Example 22

5-Methoxy-3-(methylamino)benzo[b]thiophene-2-carboxamide-1-oxide

Monomethylamine gas is passed into a room temperature solution of 5-methoxy-3-(1-methylethoxy)benzo[b]thiophene-2-carboxamide-1-oxide (250 mg, 0.89 mmol) [Boschelli, et al., U.S. Pat. No. 5,208,253 (1993)] in acetonitrile. A precipitate forms almost immediately and stirring is continued for 30 minutes. The solid is collected and dried to provide 5-methoxy-3-(methylamino)benzo[b]thiophene-2-carboxamide-1-oxide in 86% yield; mp=244°-244.5° C. dec.

Example 23

5-Methoxy-3-[(1-methylethyl)amino]benzo[b]thiophene-2-carboxamide-1-oxide

Isopropyl amine (379 μL, 4.45 mmol) is added to a room temperature solution of 5-methoxy-(3-(1-methylethoxy))benzo[b]thiophene-2-carboxamide-1-oxide (250 mg, 0.89 mmol) in 25 mL of acetonitrile. Stirring is continued for 16 hours. The reaction mixture is concentrated and recrystallized from acetonitrile to provide 5-methoxy-3-[(1-methylethyl)amino]benzo[b]thiophene-2-carboxamide-1-oxide in 64% yield; mp=193.5°-194.5° C.

Example 24

5-Methoxy-3-(phenylamino)benzo[b]thiophene-2-carboxamide-1-oxide

A mixture of 5-methoxy-(3-(1-methylethoxy))benzo[b]thiophene-2-carboxamide-1-oxide (250 mg, 0.89 mmol) and diazabicycloundecene (DBU) (664 μL, 4.4 mmol) in 5 mL of aniline is stirred at room temperature for 5 hours. The reaction mixture is diluted with ethyl acetate and washed with 1N HCl, saturated NaHCO$_3$, and brine. The organic layer is dried over MgSO$_4$, filtered, and concentrated in vacuo. Recrystallization from ethyl acetate:methanol gives 5-methoxy-3-(phenylamino)benzo[b]thiophene-2-carboxamide-1-oxide in 66% yield; mp=191°-192° C. dec.

Example 25

3-Amino-2-benzofurancarboxamide

The preparation of this compound is found in Trofimov F. A., et al., *Chem. Heterocyclic Compd.* 10, 1016 (1974).

Example 26

3-Amino-4-chloro-2-benzofurancarboxamide

The preparation of this compound is found in Beck J. R., Suhr R. G., *J. Heterocyclic Chem.* 11, 227 (1974).

Example 27

5-Methoxy-3-(1-methylethoxy)-2-benzofurancarboxamide

A solution of potassium tert-butoxide (12.0 g, 107 mmol) in 50 mL of methyl sulfoxide is cooled in a cold water bath while a solution of methyl 3-hydroxy-5-methoxy-2-benzofurancarboxylate (16.2 g, 73 mmol) [Connor D. T., et al., *J. Med. Chem.* 35, 958 (1992)] in 150 mL of methyl sulfoxide is added dropwise. The mixture is stirred for 45 minutes and 2-bromopropane (12.0 mL, 15.7 g, 128 mmol) is added in one portion. After stirring at room temperature for 48 hours, the mixture is added to 1.2 kg of ice and water and acidified with 6.0N HCl. The mixture is extracted with dichloromethane, and the combined organic layers are washed with water, 5% aqueous $Na_2CO_3$, and water again, then dried (anhydrous sodium sulfate) and evaporated to an oil residue. The oil is purified by bulb-to-bulb vacuum distillation to provide 14.2 g (74%) to methyl 5-methoxy-3-(1-methylethoxy)-2-benzofurancarboxylate, suitable for further synthesis; mp=55°-63° C.

The above ester (14.1 g, 53 mmol) is treated with lithium amide by the procedure described in Example 19 to yield 6.5 g (49%) of amide product after recrystallization from aqueous ethanol; mp=125°-127° C.

Example 28

5-Chloro-3-(1-methylethoxy)-2-benzofurancarboxamide

To 5-chloro-3-(1-methylethoxy)-2-benzofurancarboxylic acid (200 mg, 0.79 mmol) in 5 mL of dry tetrahydrofuran is added 1,1'-carbonyldiimidazole (167 mg, 1.03 mmol). The reaction solution is heated at reflux for 1 hour then cooled to room temperature. Aqueous ammonium hydroxide (3 mL) is added and the reaction mixture is stirred at room temperature overnight. The reaction is diluted with ethyl acetate and washed with 1N HCl, saturated aqueous sodium bicarbonate, and brine. The organic phase is dried over magnesium sulfate, filtered, and concentrated in vacuo to provide 5-chloro-3-(1-methylethoxy)-2-benzofurancarboxamide in 84% yield; mp=154°-155° C.

Example 29

3-(1-Methylethoxy)-2-benzofurancarboxamide

A suspension of 3-(1-methylethoxy)-2-benzofurancarboxylic acid (200 mg, 0.91 mmol) and 1,1'-carbonyldiimidazole (191 mg, 1.18 mmol) in 5 mL of tetrahydrofuran is heated at reflux for 1 hour. The reaction solution is cooled to room temperature and aqueous ammonium hydroxide (3 mL) is added and the reaction mixture is stirred at room temperature for 2 hours. The reaction is diluted with ethyl acetate and washed with 1N HCl, saturated aqueous $NaHCO_3$, and brine. The organic phase is dried over magnesium sulfate, filtered, and concentrated in vacuo. Chromatography eluting with ethyl acetate:hexane (1:1) provides 3-(1-methylethoxy)-2-benzofurancarboxamide in 77% yield; mp=82°-83° C.

Example 30

5-Methoxy-3-(1-methylethoxy)-N-(phenylmethyl)-2-benzofurancarboxamide

A solution of 5-methoxy-3-(1-methylethoxy)-2-benzofurancarboxylic acid (250 mg, 1.00 mmol) [Connor, et al., *J. Med. Chem.* 35, 935(1992)] and 1,1'-carbonyldiimidazole (211 mg, 1.30 mmol) in 7 mL of tetrahydrofuran is heated at reflux for 1 hour. The reaction solution is cooled to room temperature and benzylamine (0.66 mL, 6.00 mmol) is added and the reaction mixture is stirred at room temperature overnight. The reaction is diluted with ethyl acetate and washed with brine. The organic phase is dried over magnesium sulfate, filtered, and concentrated in vacuo. Chromatography eluting with ethyl acetate:hexane (1:3 to 1:1) provides 5-methoxy-3-(1-methylethoxy)-N-(phenylmethyl)-2-benzofurancarboxamide in 79% yield; mp=68°-69° C.

Example 31

5-Chloro-3-(1-methylethoxy)-N-phenyl-2-benzofurancarboxamide

To 5-chloro-3-(1-methylethoxy)-2-benzofurancarboxylic acid (250 mg, 0.98 mmol) in 5 mL of dry tetrahydrofuran is added oxalyl chloride (0.10 mL, 1.18 mmol) followed by dimethylformamide (0.02 mL). The solution is stirred at room temperature for 1.75 hours, then aniline (0.54 mL, 5.88 mmol) is added. The solution is stirred at room temperature overnight then partitioned between ethyl acetate and 1N HCl. The organic layer is washed with saturated aqueous $NaHCO_3$, followed by brine. The organic layer is dried over magnesium sulfate, filtered, and concentrated in vacuo. The crude product is purified by flash chromatography eluting with 3:1 hexane:ethyl acetate to provide 5-chloro-3-(1-methylethoxy)-N-phenyl-2-benzofurancarboxamide, 86% yield; mp=147°-149° C.

Example 32

5-Chloro-3-(1-methylethoxy)-N-(phenylmethyl)-2-benzofurancarboxamide

A solution of 5-chloro-3-(1-methylethoxy)-2-benzofurancarboxylic acid (250 mg, 0.98 mmol) and 1,1'-carbonyldiimidazole (206 mg, 1.27 mmol) in 5 mL of tetrahydrofuran is heated at reflux for 1 hour. The reaction solution is cooled to room temperature and benzylamine (0.64 mL, 5.88 mmol) is added and stirring is continued at room temperature overnight. The reaction is diluted with ethyl acetate and washed with brine. The organic phase is dried over magnesium sulfate, filtered, and concentrated in vacuo. Chromatography eluting with ethyl acetate:hexane (1:2) provides 5-chloro-3-(1-methylethoxy)-N-(phenylmethyl)-2-benzofurancarboxamide in 79% yield; mp=80°-82° C.

Example 33

3-(1-Methylethoxy)-N-(1-methylethyl)-2-benzofurancarboxamide

A solution of 3-(1-methylethoxy)-2-benzofurancarboxylic acid (250 mg, 1.14 mmol) and 1,1'-carbonyldiimidazole (240 mg, 1.48 mmol) in 7 mL of tetrahydrofuran is heated at reflux for 1 hour. The reaction solution is cooled to room temperature and i-propylamine (0.58 mL, 6.84 mmol) is added and the reaction mixture is stirred at room temperature for 30 minutes. The reaction is diluted with ethyl acetate and washed with brine. The organic phase is dried over magnesium sulfate, filtered, and concentrated in vacuo. Chromatography eluting with ethyl acetate:hexane (1:2 to 1:1) provides 3-(1-methylethoxy)-N-(1-methylethyl)-2-benzofurancarboxamide in 72% yield as a yellow oil.

Example 34

3-(1-Methylethoxy)-N-phenyl-2-benzofurancarboxamide

To 3-(1-methylethoxy)-2-benzofurancarboxylic acid (200 mg, 0.91 mmol) in 7 mL of dry tetrahydrofuran is added oxalyl chloride (0.095 mL, 1.09 mmol) followed by dimethylformamide (0.02 mL). The solution is stirred at room temperature for 1.75 hours, then aniline (0.50 mL, 5.46 mmol) is added. The solution is stirred at room temperature overnight then partitioned between ethyl acetate and 1N HCl. The organic layer is washed with saturated aqueous NaHCO₃ and brine. The organic layer is dried over magnesium sulfate, filtered, and concentrated in vacuo. The crude product is purified by flash chromatography eluting with 4:1 hexane:ethyl acetate to provide 5-chloro-3-(1-methylethoxy)-N-phenyl-2-benzofurancarboxamide in 84% yield; mp=82°-83° C.

Example 35

3-(1-Methylethoxy)-N-(phenylmethyl)-2-benzofurancarboxamide

A solution of 3-(1-methylethoxy)-2-benzofurancarboxylic acid (250 mg, 1.14 mmol) and 1,1'-carbonyldiimidazole (240 mg, 1.48 mmol) in 7 mL of tetrahydrofuran is heated at reflux for 1 hour. The reaction solution is cooled to room temperature and benzylamine (0.75 mL, 6.84 mmol) is added and the reaction mixture is stirred at room temperature overnight. The reaction is diluted with ethyl acetate and washed with brine. The organic phase is dried over magnesium sulfate, filtered, and concentrated in vacuo. Chromatography eluting with ethyl acetate:hexane (1:4 to 1:3) provides 3-(1-methylethoxy)-N-(phenylmethyl)-2-benzofurancarboxamide in 78% yield as a yellow oil.

Example 36

5-Methoxy-3-(phenylmethoxy)-2-benzofurancarboxamide

A suspension of 5-methoxy-3-(phenylmethoxy)-2-benzofurancarboxylic acid (157 mg, 0.50 mmol) and 1,1'-carbonyldiimidazole (96 mg, 0.59 mmol) in 15 mL of tetrahydrofuran is heated at reflux for 1.5 hours. The reaction solution is cooled to room temperature, aqueous ammonium hydroxide (1 mL) is added and the reaction mixture is stirred at room temperature for 1 hour. The reaction is diluted with ethyl acetate and washed with brine. The organic phase is dried over magnesium sulfate, filtered, and concentrated in vacuo. Chromatography eluting with ethyl acetate:hexane (1:1) provides 5-methoxy-3-(phenylmethoxy)-2-benzofurancarboxamide in 47% yield; mp=70°-72° C.

Example 37

3-(1-Methylethoxy)-5-phenyl-2-benzofurancarboxamide

A suspension of 3-(1-methylethoxy)-5-phenyl-2-benzofurancarboxylic acid (173 mg, 0.58 mmol) and 1,1'-carbonyldiimidazole (116 mg, 0.72 mmol) in 10 mL of tetrahydrofuran is heated at reflux for 2 hours. The reaction solution is cooled to room temperature and aqueous ammonium hydroxide (1 mL) is added and the reaction mixture is stirred at room temperature for 30 minutes. The reaction is diluted with ethyl acetate and washed with brine. The organic phase is dried over magnesium sulfate, filtered, and concentrated in vacuo. Chromatography eluting with ethyl acetate:hexane (1:1) provides 3-(1-methylethoxy)-5-phenyl-2-benzofurancarboxamide in 94% yield; mp=192°-130° C.

Preparative Example 7

3-(1-Methylethoxy)-5-(phenylmethoxy)-2-benzofurancarboxyic acid

A mixture of methyl 2-hydroxy-5-(phenylmethoxy)-benzoate (11.8 g, 46 mmol) [Ellis R. C., et al., *J. Chem. Soc. Perkin Trans.* 1, 1377 (1976)], methyl bromoacetate (5.7 mL, 9.2 g, 60 mmol), and potassium carbonate (8.5 g, 62 mmol) in 300 mL of N,N-dimethylformamide is stirred at room temperature for 48 hours, then cooled in ice and filtered. The insoluble material is washed with water and recrystallized from ethyl acetate-hexane to yield 12.4 g (82%) of intermediate methyl 2-(2-methoxy-2-oxoethoxy)-5-(phenylmethoxy)benzoate as a solid of mp=59°-62° C.

A solution of the above diester (9.0 g, 27 mmol) in 200 mL of dry toluene is treated with potassium tert-butoxide (3.7 g, 33 mmol), and the resulting mixture is stirred at reflux for 16 hours. The reaction mixture is cooled and the precipitated product filtered and recrystallized from ethyl acetate-hexane to yield 6.2 g (77%) of intermediate methyl 3-hydroxy-5-(phenylmethoxy)-2-benzofurancarboxylate as a solid of mp=139°-141° C.

A solution of the above benzofuran ester (5.0 g, 17 mmol) in 200 mL of tetrahydrofuran is treated with 1,8-diazabicyclo[5.4.0]undecene-7-ene (3.8 mL, 3.9 g, 25 mmol) and 2-bromopropane (2.4 mL, 6.2 g, 51 mmol). The resulting mixture is stirred at reflux for 16 hours, then cooled, and evaporated. The residue is dissolved in ethyl acetate, and the solution is washed with saturated ammonium chloride solution and brine. The organic layer is dried (anhydrous magnesium sulfate) and evaporated. Purification of the residue by flash chromatography (silica gel, 20% ethyl acetate in hexane elution) gives 3.7 g (65%) of intermediate methyl 3-(1-methylethoxy)-5-(phenylmethoxy)-2-benzofurancarboxylate as an oil suitable for further synthesis.

A mixture of the above oil (0.61 g, 1.8 mmol) and 20 mL of 2.0N aqueous sodium hydroxide solution in 20 mL of methanol is stirred at 60° C. for 2 hours. The cooled reaction mixture is added to 100 g of ice and water and acidified with 2.0N HCl. The mixture is extracted with ethyl acetate, and the combined organic layers are washed with brine, dried (anhydrous magnesium sulfate), and evaporated. Recrystallization of the residue from ethyl acetate-hexane gives 0.48 g (83%) of benzofuran acid product; mp=178°-179° C.

3-(1-Methylethoxy)-5-(phenylmethoxy)-2-benzofurancarboxamide

A mixture of 3-(1-methylethoxy)-5-(phenylmethoxy)-2-benzofurancarboxylic acid (0.53 g, 1.6 mmol) and 1,1'-carbonyldiimidazole (0.29 g, 1.8 mmol) in 20 mL of tetrahydrofuran is stirred at reflux for 2 hours. The cooled reaction mixture is treated with 3.0 mL of ammonium hydroxide solution and stirred at room temperature for an additional 2 hours. The reaction mixture is diluted with water and extracted with ethyl acetate. The combined organic layers are washed with brine, dried (anhydrous magnesium sulfate), and evaporated. Purification of the residue by flash chromatography (silica gel, 50% ethyl acetate in hexane elution) gives 0.27 g (53%) of product; mp=158°-160° C.

Example 38

5-Hydroxy-3-(1-methylethoxy)-2-benzofurancarboxamide

A solution of 3-(1-methylethoxy)-5-(phenylmethoxy)-2-benzofurancarboxamide (0.50 g, 1.5 mmol) in 75 mL of methanol is treated with 20% palladium on carbon catalyst (0.25 g) and hydrogenated for 2 hours at 50 psi hydrogen pressure. The reaction mixture is filtered and the filtrate evaporated. Recrystallization of the residue from aqueous methanol yields 0.28 g (78%) of product; mp=183°–185° C.

We claim:

1. A method of treating diseases mediated by inhibiting the adhesion of leukocytes to endothelial cells selected from the group consisting of rheumatoid arthritis, asthma and psoriasis comprising administering to a host in need thereof a therapeutically effective amount in unit dosage form of a compound of the formula

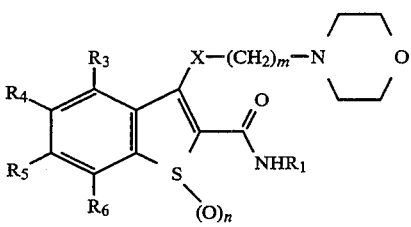

wherein $R_1$ is hydrogen; lower alkyl, or lower alkyl substituted by halogen; phenyl, or phenyl substituted by hydroxy, halogen, lower alkyl, lower alkoxy, or $CO_2R_7$ where $R_7$ is hydrogen or lower alkyl; benzyl, or benzyl substituted by hydroxy, halogen, lower alkyl, lower alkoxy, or $CO_2R_7$ as defined above;

n is an integer from 0 to 2;

m is an integer from 0 to 6;

X is $S(O)_n$ or $NR_2$ in which $R_2$ is hydrogen, lower alkyl, phenyl, benzyl, substituted lower alkyl as defined above, substituted phenyl as defined above, substituted benzyl as defined above; and $R_3$, $R_4$, $R_5$, and $R_6$ are each independently hydrogen, hydroxy, halogen, lower alkyl, trifluoromethyl, lower alkoxy, phenyl, benzyloxy, nitro, or —$NR_7R_2$ in which $R_7$ and $R_2$ are as defined above;

or a pharmaceutically acceptable acid addition or base salt thereof.

2. The method of claim 1, wherein $R_1$ is hydrogen, lower alkyl, phenyl, or benzyl in which phenyl or benzyl is unsubstituted or substituted by —$CO_2R_7$.

3. The method of claim 2, wherein the compound is carboxamide, 5-methoxy-3-[[2-(4-morpholinyl)ethyl]thio]benzo[b]thiophene-2-carboxamide.

* * * * *